United States Patent
Gatzemeyer et al.

(10) Patent No.: US 8,201,295 B2
(45) Date of Patent: Jun. 19, 2012

(54) ORAL CARE IMPLEMENT HAVING USER-INTERACTIVE DISPLAY AND MOVING HEAD

(75) Inventors: John J. Gatzemeyer, Hillsborough, NJ (US); Eduardo J. Jimenez, Manalapan, NJ (US); Robert Riebe, Minneapolis, MN (US); Paul Fair, Denver, CO (US); James E. Michaels, Downers Grove, IL (US); Evan Ward, Chicago, IL (US)

(73) Assignee: Colgate-Palmolive Company, New York, NY (US)

( * ) Notice: Subject to any disclaimer, the term of this patent is extended or adjusted under 35 U.S.C. 154(b) by 1024 days.

(21) Appl. No.: 11/676,050

(22) Filed: Feb. 16, 2007

(65) Prior Publication Data

US 2008/0196185 A1 Aug. 21, 2008

(51) Int. Cl.
 *A46B 13/02* (2006.01)
 *A61C 17/22* (2006.01)
(52) U.S. Cl. .......................................... 15/22.1; 15/105
(58) Field of Classification Search .................. 15/22.1, 15/28, 105
 See application file for complete search history.

(56) References Cited

U.S. PATENT DOCUMENTS

| | | | |
|---|---|---|---|
| 4,207,087 A | 6/1980 | Morrison et al. | |
| 5,232,370 A | 8/1993 | Hoye | |
| 5,544,382 A | 8/1996 | Giuliani et al. | |
| 5,673,451 A | 10/1997 | Moore et al. | |
| 5,810,601 A | 9/1998 | Williams | |
| 5,864,288 A | 1/1999 | Hogan | |
| 5,875,796 A | 3/1999 | Silver-Isenstadt et al. | |
| 5,924,159 A | 7/1999 | Haitin | |
| 5,930,858 A * | 8/1999 | Jung ........................... 15/22.1 | |
| 5,943,723 A | 8/1999 | Hilfinger et al. | |
| 5,944,531 A | 8/1999 | Foley et al. | |
| 6,154,912 A | 12/2000 | Li | |
| 6,199,239 B1 | 3/2001 | Dickerson | |
| 6,202,242 B1 | 3/2001 | Salmon et al. | |
| 6,389,633 B1 | 5/2002 | Rosen | |
| 6,442,787 B2 | 9/2002 | Hohlbein | |
| 6,461,238 B1 | 10/2002 | Rehkemper et al. | |
| 6,536,068 B1 | 3/2003 | Yang et al. | |
| 6,611,780 B2 | 8/2003 | Lundell et al. | |
| 6,731,213 B1 | 5/2004 | Smith | |
| 6,754,928 B1 | 6/2004 | Rosen | |

(Continued)

FOREIGN PATENT DOCUMENTS

CA 2 232 528 9/1999

(Continued)

OTHER PUBLICATIONS

International Search Report Dated Jul. 3, 2008.

(Continued)

*Primary Examiner* — Randall Chin
(74) *Attorney, Agent, or Firm* — Amy M. Fernandez

(57) ABSTRACT

An oral care implement includes a display and/or a plurality of other lighted regions, together with an element for inducing motion in a head region. The display and/or lights are used to provide instructions to the user regarding a periodically-performed oral care regimen. The motion-inducing element can be pulsed or otherwise selectively activated to signal different intervals in the regimen. Upon successful conclusion of the oral care regimen, the lights and/or display and the motion-inducing element are used to provide a game or other entertainment to the user.

21 Claims, 20 Drawing Sheets

U.S. PATENT DOCUMENTS

| | | |
|---|---|---|
| 6,802,097 B2 | 10/2004 | Hafliger et al. |
| 6,850,167 B2 | 2/2005 | Rosen |
| 6,954,961 B2 | 10/2005 | Ferber et al. |
| 7,003,839 B2 | 2/2006 | Hafliger et al. |
| 7,448,109 B2 * | 11/2008 | Brewer et al. .................. 15/22.1 |
| 2001/0034917 A1 | 11/2001 | DuCey |
| 2001/0050507 A1 | 12/2001 | Boucherie |
| 2003/0017874 A1 | 1/2003 | Jianfei et al. |
| 2003/0063011 A1 | 4/2003 | Rosen |
| 2003/0115694 A1 | 6/2003 | Pace |
| 2003/0205492 A1 | 11/2003 | Ferber et al. |
| 2004/0134000 A1 | 7/2004 | Hilfinger et al. |
| 2005/0091769 A1 | 5/2005 | Jimenez et al. |
| 2005/0229345 A1 | 10/2005 | Rouse et al. |
| 2006/0037158 A1 | 2/2006 | Foley et al. |
| 2006/0040246 A1 | 2/2006 | Ding et al. |
| 2006/0117508 A1 | 6/2006 | Hohlbein |
| 2006/0257822 A1 | 11/2006 | Ghosh et al. |
| 2007/0094822 A1 | 5/2007 | Gatzerneyer |
| 2007/0136964 A1 | 6/2007 | Dawley |
| 2007/0270221 A1 | 11/2007 | Park et al. |
| 2008/0109973 A1 | 5/2008 | Farrell et al. |
| 2009/0143914 A1 * | 6/2009 | Cook et al. .................... 700/275 |

FOREIGN PATENT DOCUMENTS

| | | |
|---|---|---|
| CN | 2299526 | 12/1998 |
| CN | 1416759 | 5/2003 |
| CN | 2633244 | 8/2004 |
| CN | 2685937 | 3/2005 |
| CN | ZL 200420014704.6 | 3/2005 |
| DE | 3935554 A1 | 5/1991 |
| DE | 4029770 A1 | 3/1992 |
| DE | 195 06 129 | 8/1996 |
| DE | 299 15 858 | 9/1999 |
| DE | 100 01 502 | 3/2001 |
| DE | 100 26 513 | 5/2001 |
| DE | 100 45 353 | 3/2002 |
| DE | 101 20 090 * | 8/2002 |
| DE | 101 54 946 | 5/2003 |
| DE | 10247698 A1 | 4/2004 |
| DE | 102006005205 A1 | 9/2006 |
| FR | 2544602 | 11/1986 |
| FR | 2724298 A1 | 3/1996 |
| JP | 8-19427 A | 1/1996 |
| JP | 2002369718 | 12/2002 |
| JP | 2003310644 | 11/2003 |
| RU | 2098993 | 12/1997 |
| RU | 2174381 C2 | 10/2001 |
| WO | 2006065159 A2 | 6/2006 |
| WO | WO 2006/137648 | 12/2006 |
| WO | WO 2007/072430 | 6/2007 |
| WO | WO 2007/097886 | 8/2007 |

OTHER PUBLICATIONS

International Search Report from the International Searching Authority (EP) for International Application No. PCT/US2007/087134 dated Mar. 25, 2008.

Examiner's First Report from the Patent Office of Australia for corresponding Australian Patent Application No. 2008216204 dated Sep. 23, 2010.

Search Report from the Intellectual Property Office of Taiwan for corresponding Tawian Patent Application No. 097105282 dated Jan. 26, 2011.

Examination Report from the National Office of Intellectual Property of Vietnam for corresponding Vietnamese Patent Application No. 1-2009-01946 dated Mar. 23, 2011.

First Office Action from the Chinese Patent Office, dated Mar. 22, 2011, relating to corresponding Chinese Patent Application No. 200880011930.X, filed on Feb. 14, 2008.

Decision on Grant from the Russian Patent Office, dated Apr. 13, 2011, relating to corresponding Russian Patent Application No. 2009134540, filed on Feb. 14, 2008.

* cited by examiner

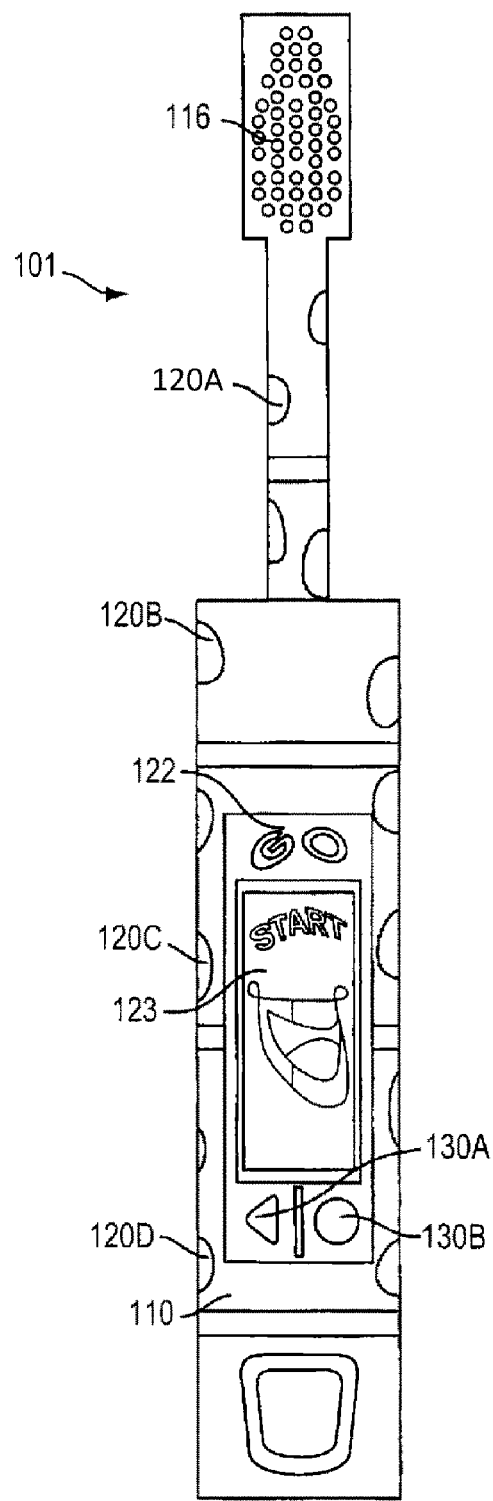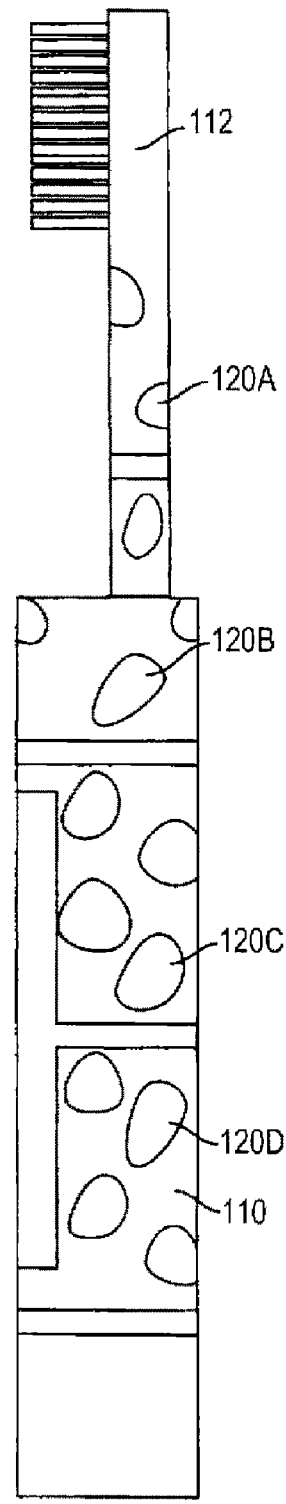
FIG. 2A                    FIG. 2B

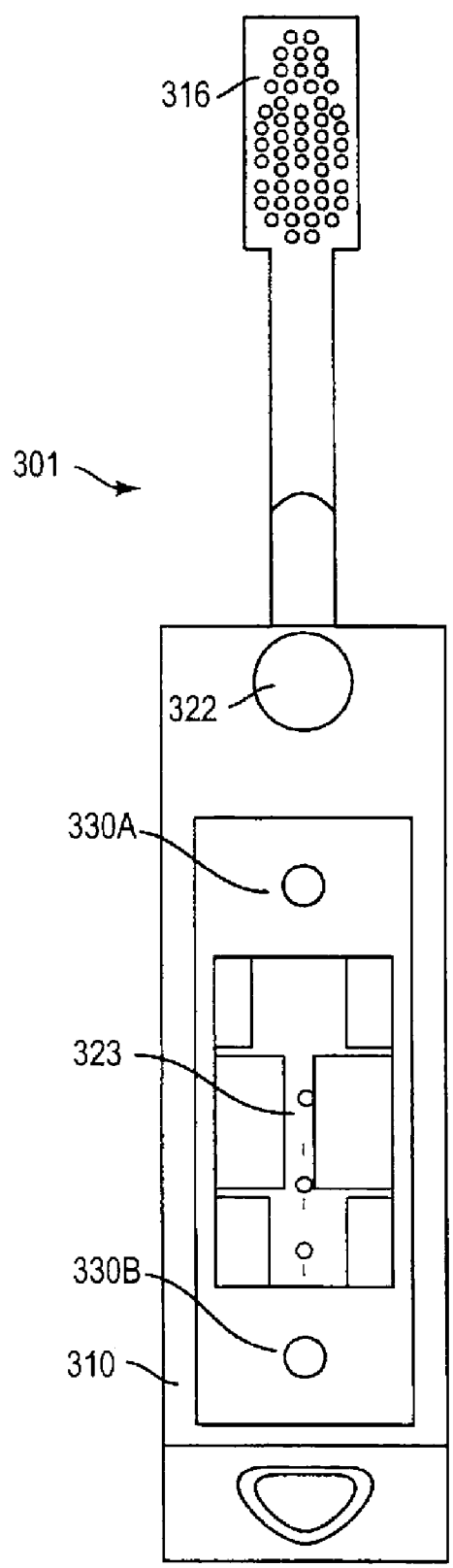
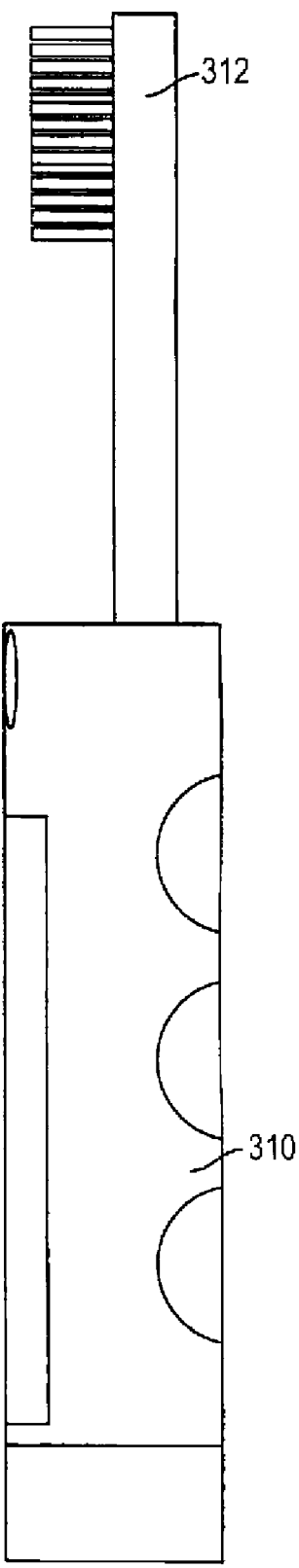
FIG. 4A
FIG. 4B

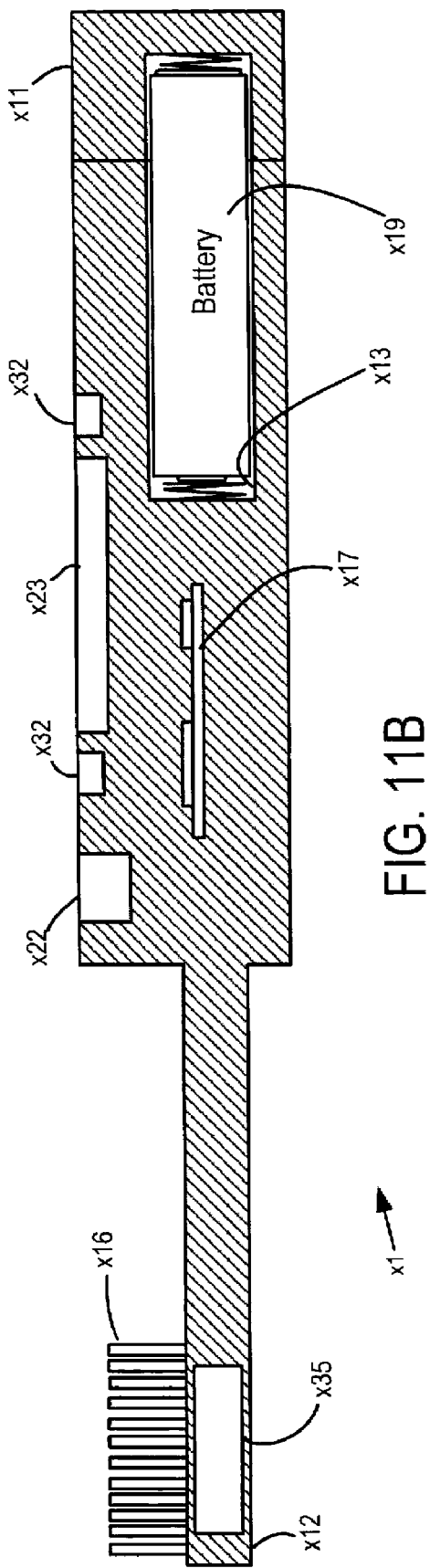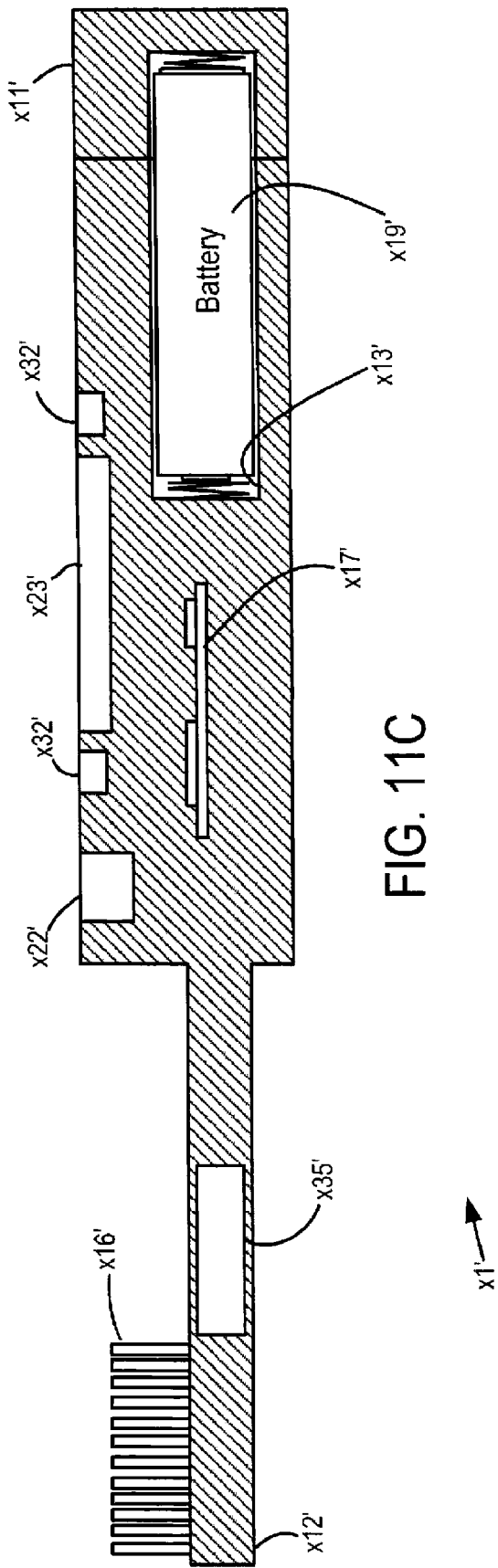

ORAL CARE IMPLEMENT HAVING USER-INTERACTIVE DISPLAY AND MOVING HEAD

FIELD OF THE INVENTION

The present invention pertains to an oral care implement that provides an entertaining and/or educational interactive competition using a vibratory or motion inducing device.

BACKGROUND OF THE INVENTION

Dentists generally recommend that an individual brush his or her teeth for a minimum interval per cleaning, such as two minutes. Despite such recommendations, many individuals, especially young children, do not regularly brush their teeth for the recommended minimum interval. Such habits often can be attributed to the individual regarding tooth brushing as a mundane duty with few pleasurable aspects.

A toothbrush that shows an example of brushing behavior reinforcement is described in U.S. Pat. No. 6,389,633 to Rosen. A motion sensing means is used to monitor the brushing action of the user. When the logic requirements of motion sensing are complete, the logic means directs a digital output display means to output to a small LCD screen or speaker a visual and/or an audible indication to the user, such as in the form of a rudimentary game or congratulatory message.

Powered toothbrushes generally have a movable head that is motor-driven from a handle. While such toothbrushes usually achieve a more intensive cleaning action than manual toothbrushes, they may be uncomfortable for users due to transmission of motor vibrations to the hand of the user.

These problems are magnified in that adult powered toothbrushes may be uncomfortable for some users, such as children. Further, the differences in the oral cavity size and tooth configurations between children and adults make it difficult for children to use adult toothbrushes.

There remains a need for alternative techniques for promoting oral hygiene, and particularly for providing an incentive to users to brush their teeth for at least a minimum recommended brushing interval. Further, there is a need for an oral care implement ergonomically configured for children.

BRIEF SUMMARY OF THE INVENTION

The present invention pertains to an oral care implement that provides an entertaining and/or educational interactive competition using a vibratory or motion inducing device.

In one embodiment, an oral care implement includes a display and/or a plurality of other lighted regions, as well as a motor or other element for inducing motion in a head region of the implement.

In one embodiment, the motion inducing element may induce vibratory or oscillatory motion of tooth-cleaning elements (e.g., bristles) located in the head.

In one embodiment, the display and/or lights are used to provide instructions to the user regarding a periodically-performed oral care regimen.

In one embodiment, the lights and/or display are used to instruct a user to brush one portion of the user's teeth for a certain amount of time, then another portion of the user's teeth.

In one embodiment, the motion-inducing element can be pulsed or otherwise selectively activated to signal different intervals in the regimen.

In one embodiment, upon conclusion of the oral care regimen, the lights and/or display and the motion-inducing element are used to provide a game or other entertainment to the user.

In one embodiment, an ergonomic oral care implement is configured for the anatomical structures of children.

BRIEF DESCRIPTION OF THE DRAWINGS

The foregoing summary of the invention, as well as the following detailed description of illustrative embodiments, is better understood when read in conjunction with the accompanying drawings, which are included by way of example, and not by way of limitation with regard to the claimed invention.

FIGS. 2A and 2B are front and side views, respectively, of a toothbrush according to another embodiment.

FIGS. 4A and 4B are front and side views, respectively, of a toothbrush according to another embodiment.

FIGS. 11A-11C show internal components of toothbrushes according to at least some embodiments.

DETAILED DESCRIPTION

Figure 1A:
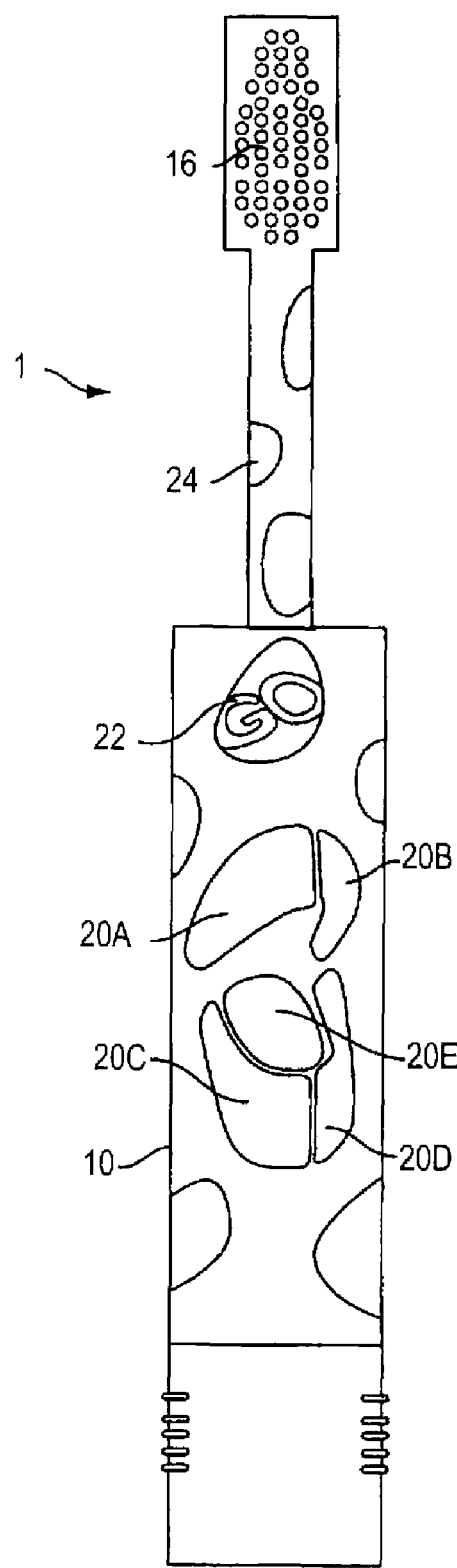
FIGS. 1A and 1B are a front and side views, respectively, of a toothbrush according to at least one embodiment.
Figure 1B:
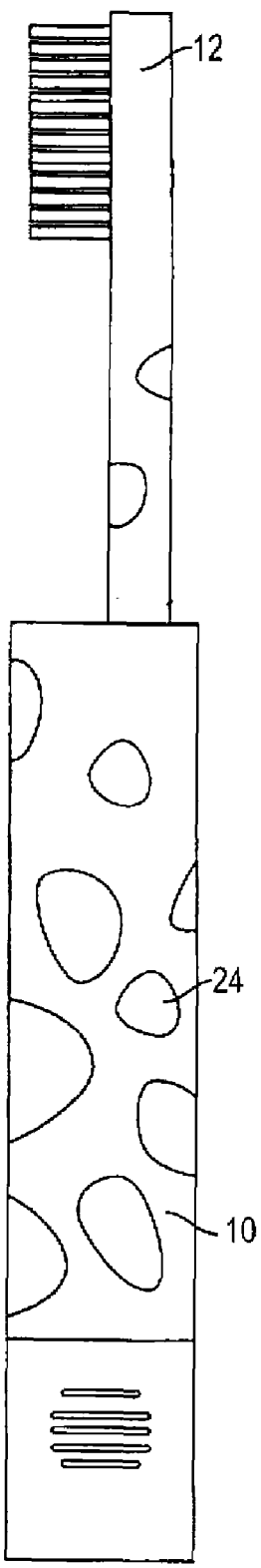

FIGS. 1A and 1B illustrate a toothbrush 1 having a handle 10 and a head 12 containing tooth cleaning elements, such as bristles 16 and/or elastomeric cleaning elements (not shown). Any bristle configuration and any handle configuration can be used, and the present invention should not be regarded as being limited to any particular configuration. Toothbrushes described and shown in other embodiments below may share these features and such description will not be repeated. For convenience, similar elements in various embodiments will be indicated in the drawings using similar reference numbers, but with 100 added to the reference numbers to distinguish between embodiments.

Toothbrush 1 is battery-powered. In addition to the lighted segments 20A-20E (described below), toothbrush 1 includes an internal motor (or other vibratory element) for generating vibration of head 12 during brushing of a user's teeth. The vibratory element of toothbrush 1 is not visible in FIGS. 1A and 1B. However, locations and configurations for the vibratory element of toothbrush 1 (and for other embodiments) are described below in connection with FIGS. 11A through 11C. Although toothbrush 1 and other embodiments include a vibratory motion-inducing element, other types of motion-inducing elements can be used. For example, and as described in connection with FIG. 12 below, an oscillatory motion-inducing element can be employed.

As shown in FIGS. 1A and 1B, lighted segments 20A-20E are shaped and arranged resemble tooth quadrants and a tongue. A button 22 is provided to enable a user to activate the functionality of the toothbrush, as described below. Toothbrush 1 optionally may include a plurality of additional lighted areas 24 at various locations of handle 10. Lighted areas 24 may be uniformly sized and spaced or, as shown in FIGS. 1A and 1B, differently sized and/or spaced. Button 22 may be similar in appearance to lighted areas 24 and optionally may be lighted. Alternatively, some or all of areas 24 may be decorative (e.g., colored and/or textured) instead of being lighted.

Lighted segments 20A-20E together resemble an open mouth, with four generally quarter-circle shaped portions 20A-20D resembling groups of teeth surrounding a generally teardrop-shaped portion 20E resembling a tongue. When a user activates toothbrush 1 by pressing button 1, the internal vibratory element of toothbrush 1 is energized and causes head 12 to vibrate. Toothbrush 1 further includes an internal memory configured, upon a user's initial press of button 22, to cause illumination of one or more of segments 20A-20E. In this manner, a user is instructed to brush in a particular brushing zone for a prescribed interval of time. Additional segments thereafter can be sequentially illuminated to instruct the user to brush in additional brushing zones. A suitable interval of time can be selected for each zone, e.g., about 30 seconds. The interval for a zone can be the same or different than the interval for other zone(s).

For example, segments 20B and 20D can be illuminated during a first 30-second interval to instruct the user to brush the outside surfaces of the top and bottom teeth, including the front and back teeth. At the conclusion of the first interval, a second 30-second interval begins during which segment 20C may be illuminated to instruct the user to brush the upper molars. At the conclusion of the second interval, segment 20A may be illuminated during a third 30-second interval to instruct the user to brush the lower molars. During a fourth 30-second interval, segment 20E may be illuminated to instruct the user to brush the tongue and the surfaces behind the teeth. A four-interval brushing regimen is described merely as one example. If desired, a different number of intervals may be chosen, such as two (e.g., upper teeth/lower teeth), three (e.g., front teeth/upper teeth/lower teeth), five (e.g., outside teeth/upper molars/lower molars/back surfaces/tongue), and so on.

After the user has completed brushing in the prescribed brushing zones, the vibratory element is deactivated, and some or all of lighted segments 20A-20E, 22 (if button 22 is lighted) and 24 can be illuminated, e.g., flashed in a random sequence. The memory can be programmed to cause such lighting for a prescribed interval of time, e.g., 15-20 seconds, as a signal that the user has completed the recommended brushing regimen. A young child will be encouraged to complete the entire brushing regimen to receive the reward of this "light show." In alternate embodiments, the vibratory element remains on and the light show continues until the user presses button 22 a second time.

Figure 1C:
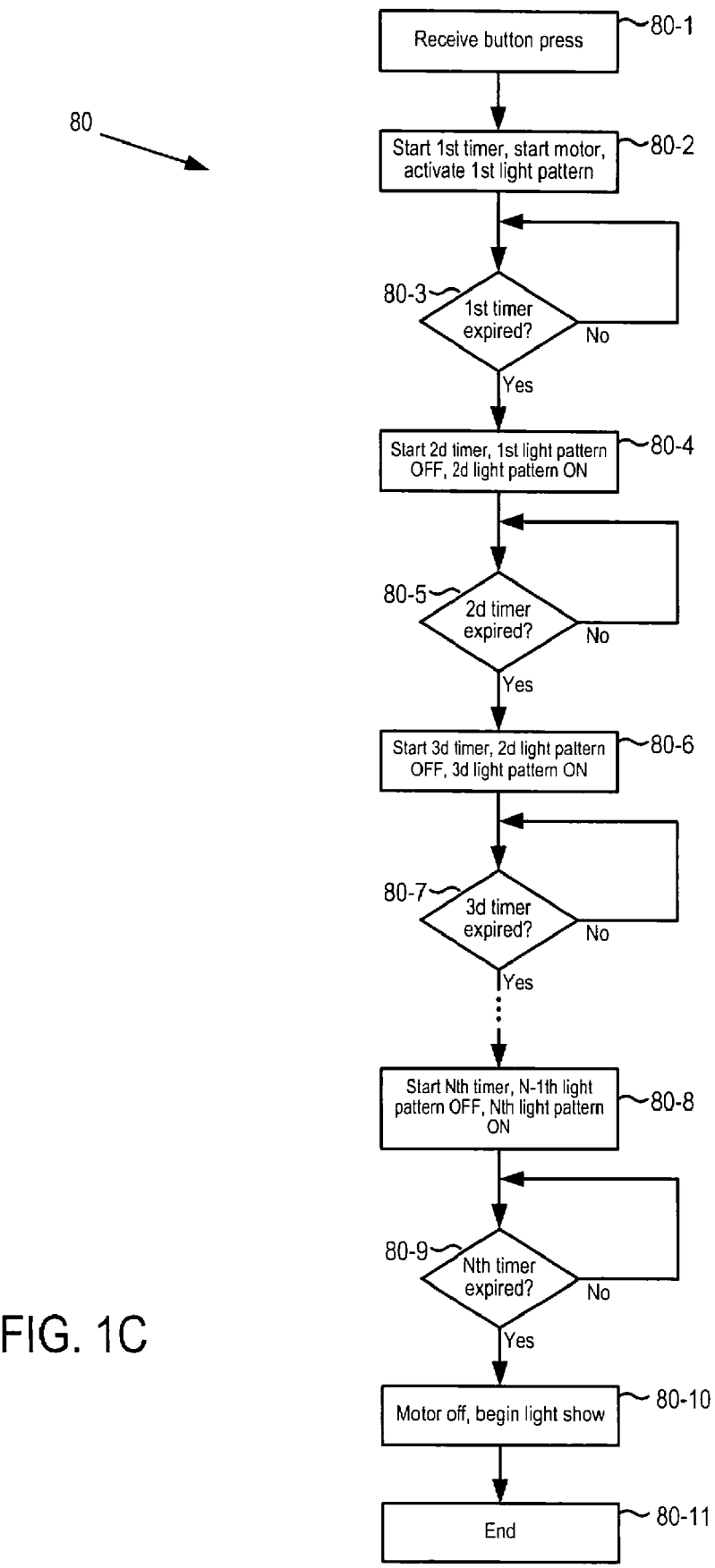
FIGS. 1C and 1D are flow charts showing operation of a toothbrush according to at least some embodiments.

FIG. 1C is a flow chart showing an algorithm 80 for operation of toothbrush 1 according to at least some embodiments. Operation begins when a user presses button 22 (block 80-1). Operation proceeds to block 80-2, where toothbrush 1 initiates a first timer period, energizes the motor (or other vibratory element) and activates a first light pattern. Using the previous example, the first timer period would be 30 seconds and the first light pattern would be illumination of light segments 20B and 20D.

Operation then proceeds to block 80-3, where toothbrush 1 determines if the first timer period has expired. If not, the operation loops back along the "no" branch. If the first timer period has expired, operation proceeds on the "yes" branch to block 80-4. In block 80-4, a second timer period is started, the first light pattern is deactivated, and a second light pattern is activated. Again using the example from above, the second timer period could be 30 seconds and the second light pattern could be illumination of segment 20C. This general pattern repeats in blocks 80-5 through block 80-9 so as to provide instruction for the entire prescribed brushing regimen. The ellipsis between blocks 80-7 and 80-8 indicate that any number timer periods and light patterns can be implemented. All timer periods need not be the same, and innumerable other light patterns could be used.

After the last timer period has expired (block 80-9), the toothbrush deactivates the motor and initiates the light show (block 80-10). From block 80-10 the operation ends at block 80-11.

Figure 1D:
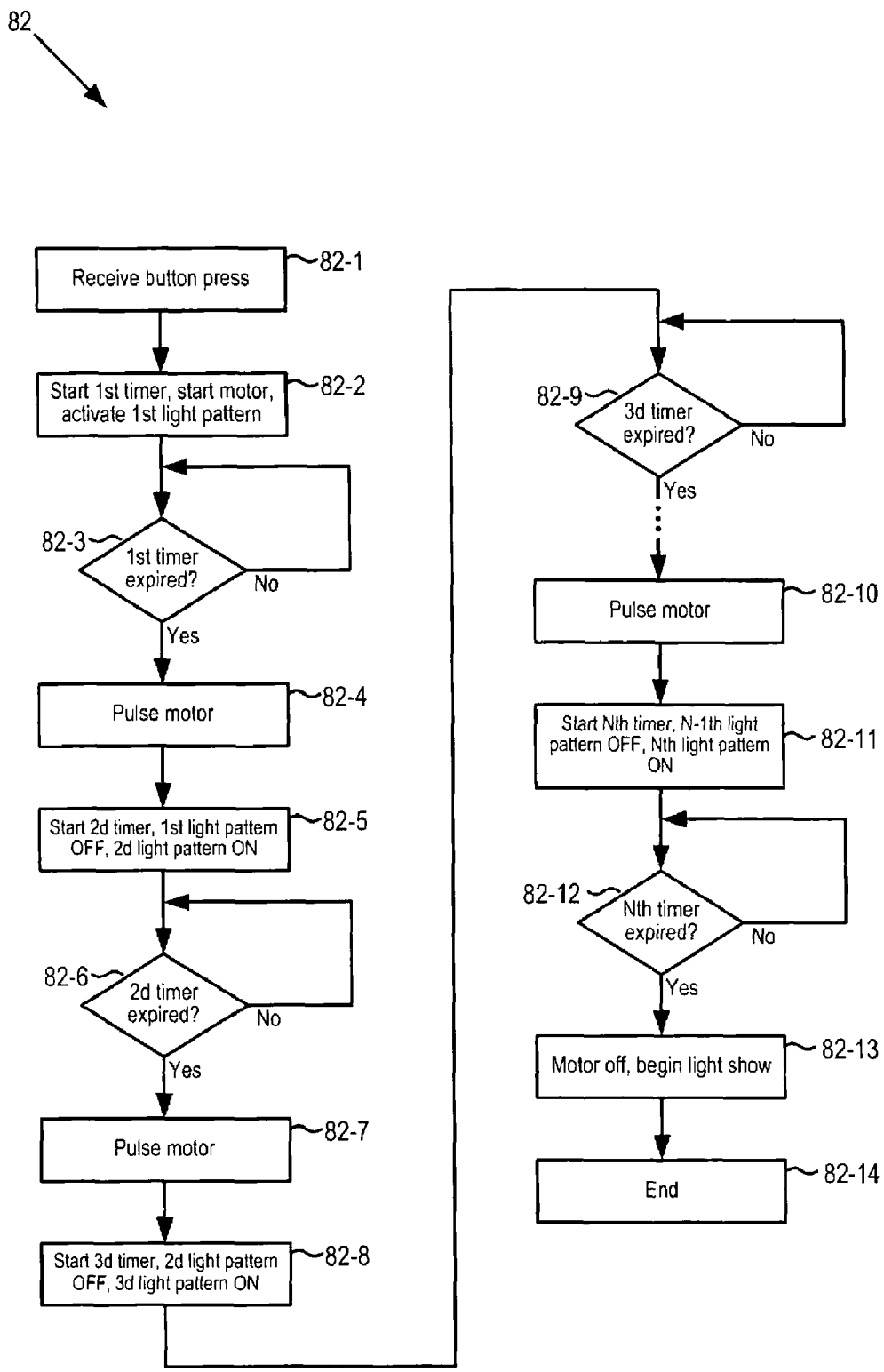

FIG. 1D is a flow chart showing another algorithm 82 for operation of toothbrush 1 according to at least some embodiments. Blocks 82-1 through 82-3, 82-5, 82-6, 82-8, 82-9 and 82-11 through 82-14 of algorithm 82 are similar to blocks 80-1 through 80-11, respectively, of algorithm 80. However, algorithm 82 differs by way of processor providing signaling to pulse the motor between each of the timer periods (blocks 82-4, 82-7 and 82-10). In this manner, a user receives a tactile cue that a new brushing regimen interval has begun (e.g., that it is time to brush another zone). In turn, this permits a user to avoid interruption of brushing to check whether a new light pattern has been engaged. Although not shown, additional pulsing intervals could be included between timer intervals represented collectively by the ellipsis in FIG. 1D.

FIGS. 2A and 2B illustrate another embodiment in which a toothbrush 101 is divided into a plurality of sections each having a plurality of lighted areas 120A, 120B, 120C, and 120D. Toothbrush 101 includes a handle 110, head 112 and cleaning elements 116 (e.g., bristles), as well an internal vibratory element (not visible in FIGS. 2A and 2B). A display screen 123 is provided for displaying graphical objects. When button 122 is pressed, the vibratory element is activated, and display screen 123 displays "start" or some other indicia that a brushing regimen is commencing. Display screen 123 also shows a graphical object representing teeth and a tongue, with a portion of the displayed teeth shaded as an instruction to brush the outside surfaces of the upper and lower teeth for a prescribed interval. Display screen 123 also may display a timer that displays the amount of time remaining in the interval, e.g., in seconds. During intervals of the brushing regimen, one or more of the lighted areas 120A-120D are caused to blink as additional indicators of the current brushing zone. At the conclusion of an interval of the regimen, a graphical object representing a subsequent brushing zone, e.g., front teeth, can be displayed while a different set of one or more of areas 120A-120D is caused to blink. This procedure can be repeated for additional brushing zones, e.g., upper molars, lower molars, etc., by displaying representative objects on display screen 123 and illuminating other lighted areas (e.g., 120B, 120A, etc.).

At the conclusion of all the prescribed brushing intervals in the regimen, all of the areas 120A-20D can be caused to blink, if desired, as a signal that brushing has been completed. Either of algorithms 80 (FIG. 1C) or 82 (FIG. 1D) can also be adapted to toothbrush 101. Such adaptation is within the routine ability of a person of having ordinary skill in the art (once such a person is provided with the information contained herein), and is therefore not discussed further.

In at least some embodiments, toothbrush 101 allows a user to play a game after a brushing regimen is completed. Display 123 can be caused to display a game, with which the user can interact via controls (e.g., additional buttons) 130A and 130B. As discussed more fully below, the game can utilize some or all of the objects displayed during brushing. For example, the user may control a "gunship" that fires shots to remove plaque from teeth. The controls 130A and 130B can be used to move the gunship left and right and to fire shots, for example. The motor can also be incorporated into the game and provide haptic feedback to the game player. As but one example, logic within toothbrush 101 may cause the motor to be briefly pulsed whenever a target is hit during game play.

As a variation of the "gunship" game, the display can be configured so that simulated plaque pieces descend from the top of the screen (e.g., which can be oriented vertically) at random lateral positions. Rectangles representing teeth are displayed across the bottom of the screen. The user controls lateral movement of a toothbrush positioned above the teeth. The object of the game is to position the toothbrush below a descending plaque piece to intercept it before it falls onto a tooth. When a plaque piece is successfully intercepted, it disappears and the user then attempts to intercept subsequent plaque pieces. The velocity and/or frequency of the falling plaque pieces can be made to increase as the game progresses to make the game more challenging the longer it is played. The game can end, for example, when a predetermined number of plaque pieces fall onto a tooth.

Figure 2C:
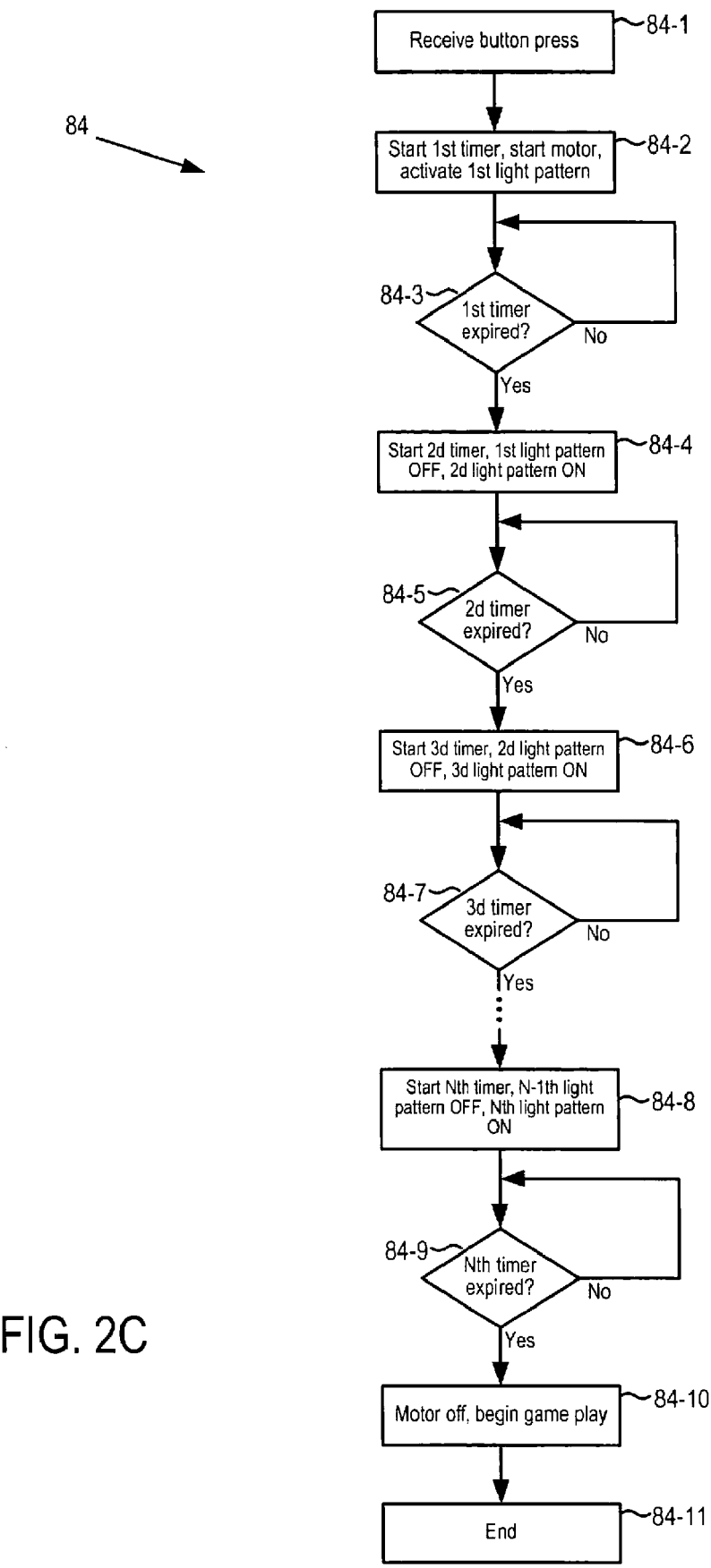
FIGS. 2C and 2D are flow charts showing operation of a toothbrush according to at least some embodiments.
Figure 2D:
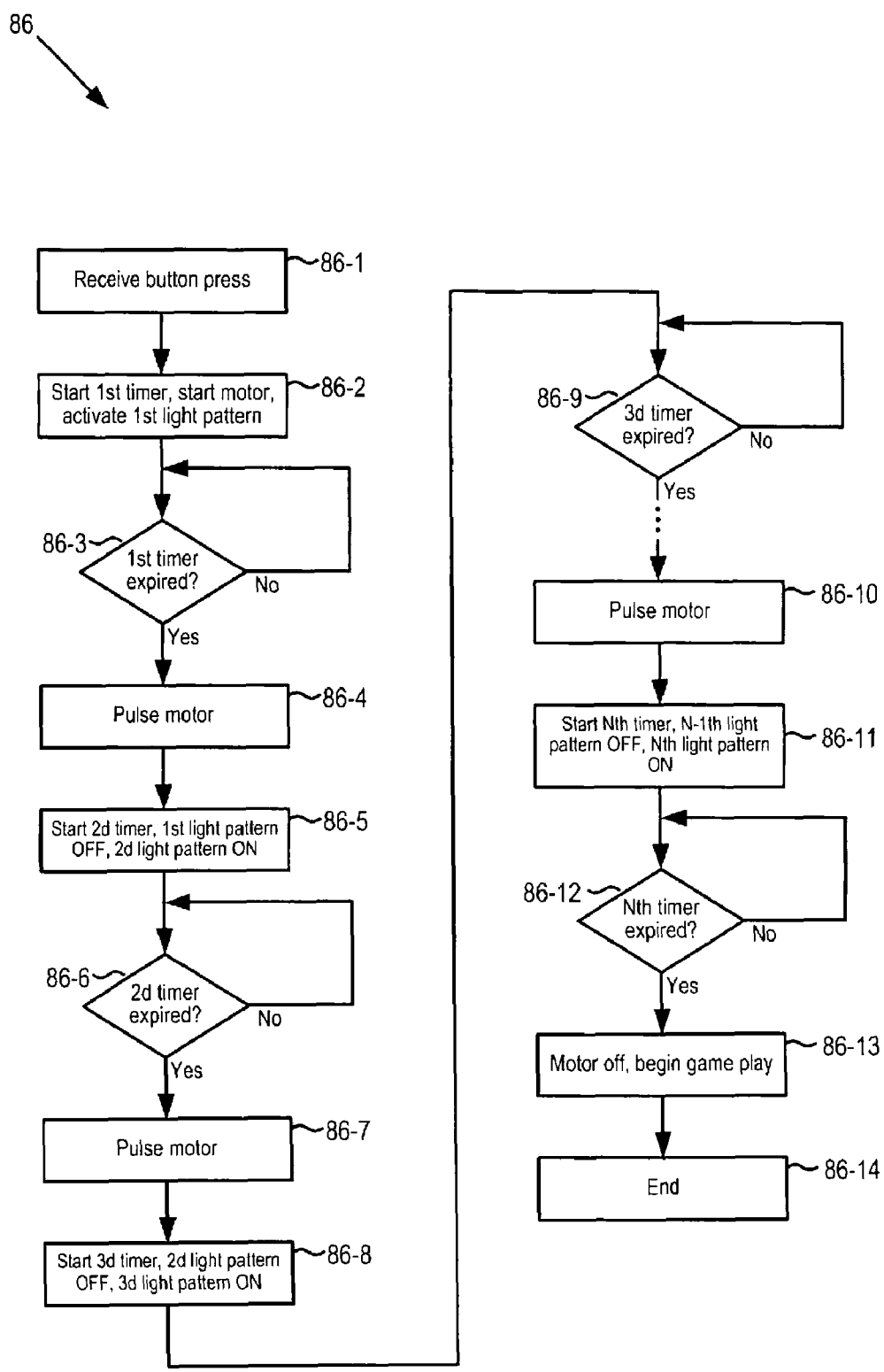

FIGS. 2C and 2D show variations of the algorithms previously described in connection with FIGS. 1C and 1D, but which are adapted to allow game play upon conclusion of a brushing regimen. Blocks 84-1 through 84-9 of algorithm 84 (FIG. 2C) are similar to blocks 80-1 through 80-9, respectively, of algorithm 80 (FIG. 1C). However, instead of providing a light show after completion of the brushing regimen (i.e., after completion of the Nth timer period), a game is initiated in block 84-10. Blocks 86-1 through 86-12 of algorithm 86 (FIG. 2D) are similar to blocks 82-1 through 82-12, respectively, of algorithm 82 (FIG. 1DC). However, instead of providing a light show after completion of the brushing regimen (i.e., after completion of the Nth timer period), a game is initiated in block 86-13. The game play in block 84-10 or in block 86-12 can be allowed to continue until the user turns off the toothbrush (e.g., by repressing button 122), or for a certain predetermined period (e.g., so a young child will not spend excessive time playing the game).

Figure 3A:
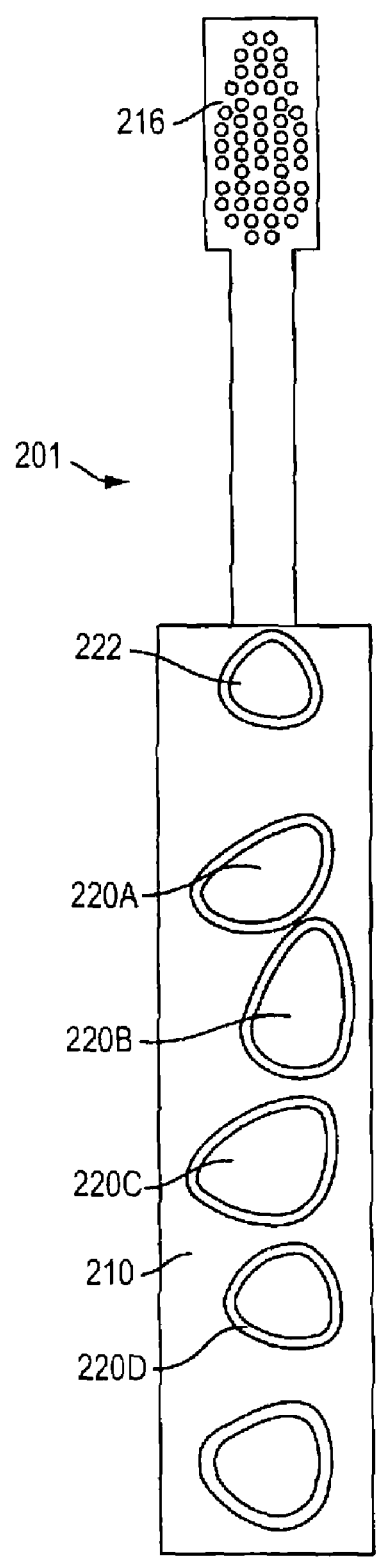
FIGS. 3A and 3B are front and side views, respectively, of a toothbrush according to another embodiment.
Figure 3B:
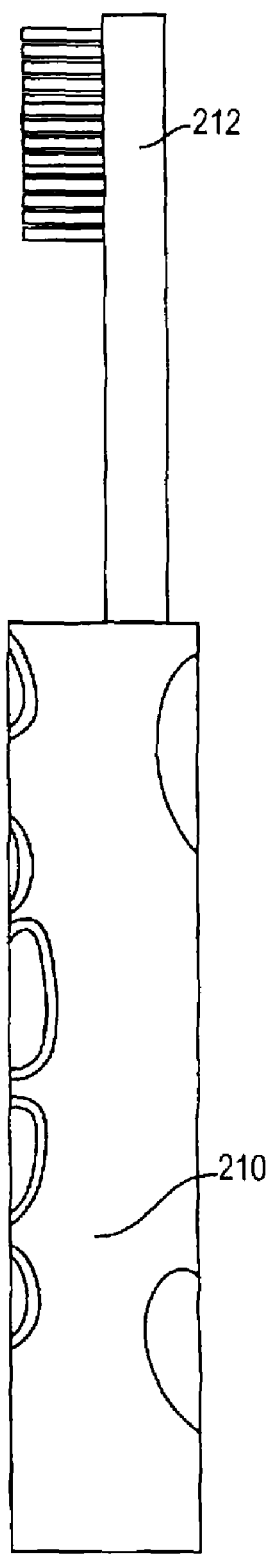

FIGS. 3A and 3B illustrate an alternative embodiment in which toothbrush 201 includes lighted buttons 220A, 220B, 220C and 220D. Lights 220A-220D provide indicators of a plurality of brushing zones, e.g., front teeth, upper molars, lower molars and tongue. Toothbrush 201 includes a handle 210, head 212 and cleaning elements 216 (e.g., bristles), as well an internal vibratory element (not visible in FIGS. 3A and 3B). After button 222 is depressed, the vibratory element activates and causes head 212 to vibrate. Buttons 220A, 220B, 220C and 220D are successively illuminated for respective brushing intervals, e.g., 30-second intervals. At the conclusion of the brushing intervals, the lighted buttons 20A, 20B, 20C and 20D can be used for a memory game. For example, two or more of the buttons 220A, 220B, 220C and 20D can be blinked in succession. The object of the game is for the user to repeat the lighting sequence. If the user correctly repeats the lighting sequence, an audible message can be played (e.g., "good job") and/or the vibratory element pulsed as a haptic indicator of success, and a more complex (e.g., longer sequence) of buttons 220A, 220B, 220C and 220D can be blinked for the next round. If the user does not correctly repeat a lighting sequence, the user may be given an additional opportunity to repeat the same sequence. Optionally, an incorrectly entered sequence can be indicated in some manner, such as by flashing all of the lighted buttons 220A, 220B, 220C and 220D together, before the sequence is repeated. Optionally, the game can end after one incorrect sequence (or alternatively two or more consecutive incorrect sequences) are entered.

FIGS. 4A and 4B show a toothbrush 301 according to another embodiment. Toothbrush 301 includes a display screen 323 and game controllers 330A and 330B. Toothbrush 301 further includes a handle 310, head 312 and cleaning elements 316 (e.g., bristles), as well an internal vibratory element (not visible in FIGS. 4A and 4B). Display screen 323 shows six generally rectangular shaped areas representative of tooth sections. Brushing intervals in a brushing regimen can be indicated by illuminating two or more of the rectangular shaped areas at a time, e.g., to indicate front teeth, upper molars, lower molars, etc. When the user presses button 322, the vibratory element is activated and vibrates head 312, and display screen 323 displays an indication of the brushing zone for a current interval. At the conclusion of the brushing intervals, display screen 323 can display a game, which can include the same graphical objects used during the brushing intervals. For example, the user can control a simulated gun character that shoots plaque off of teeth. The vibratory element can similarly be incorporated into the game to provide haptic feedback. In this way, incorporating educational oral care concepts into virtual graphical entities (e.g., simulated teeth and plaque) that the player can battle has the effect of making the game play more engaging and entertaining to promote good brushing habits.

Figure 5A:
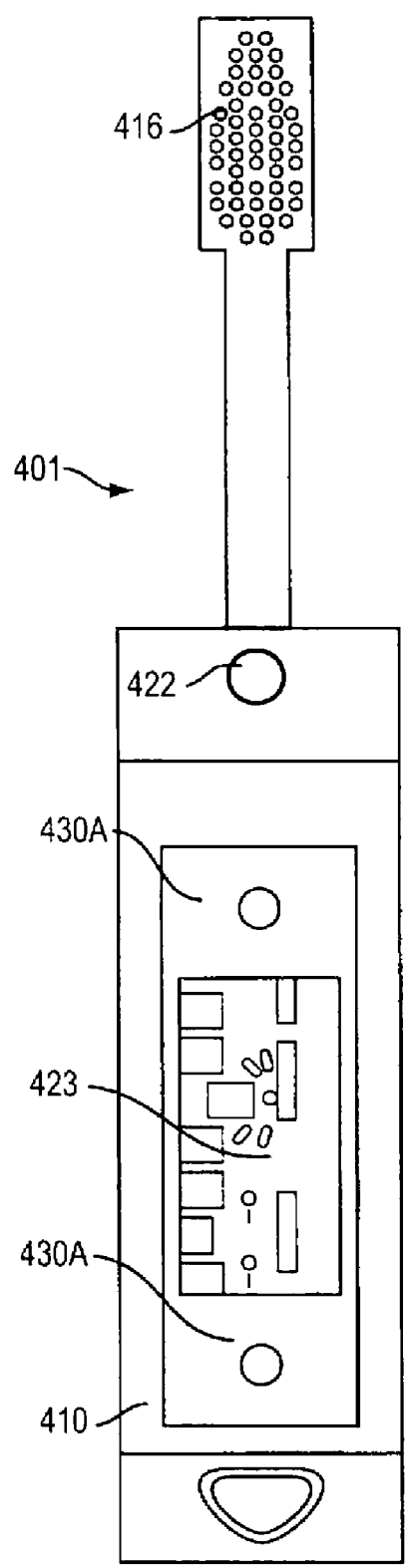
FIGS. 5A and 5B are front and side views, respectively, of a toothbrush according to another embodiment.
Figure 5B:
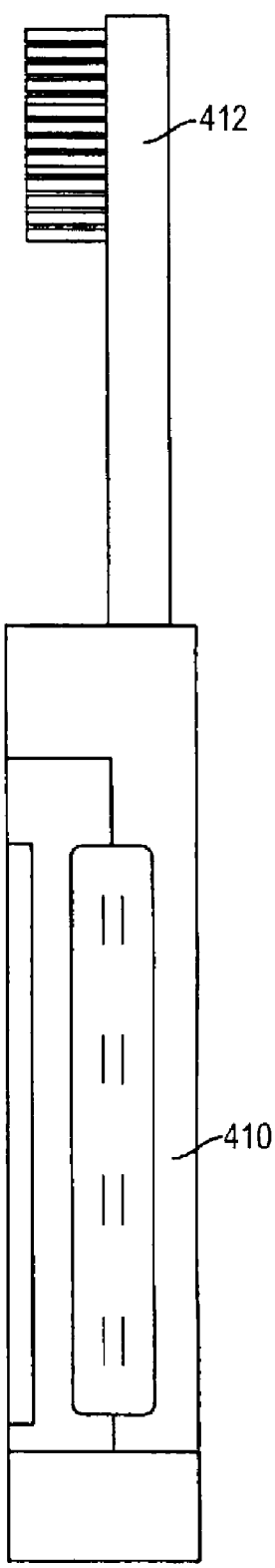
Figure 5C:
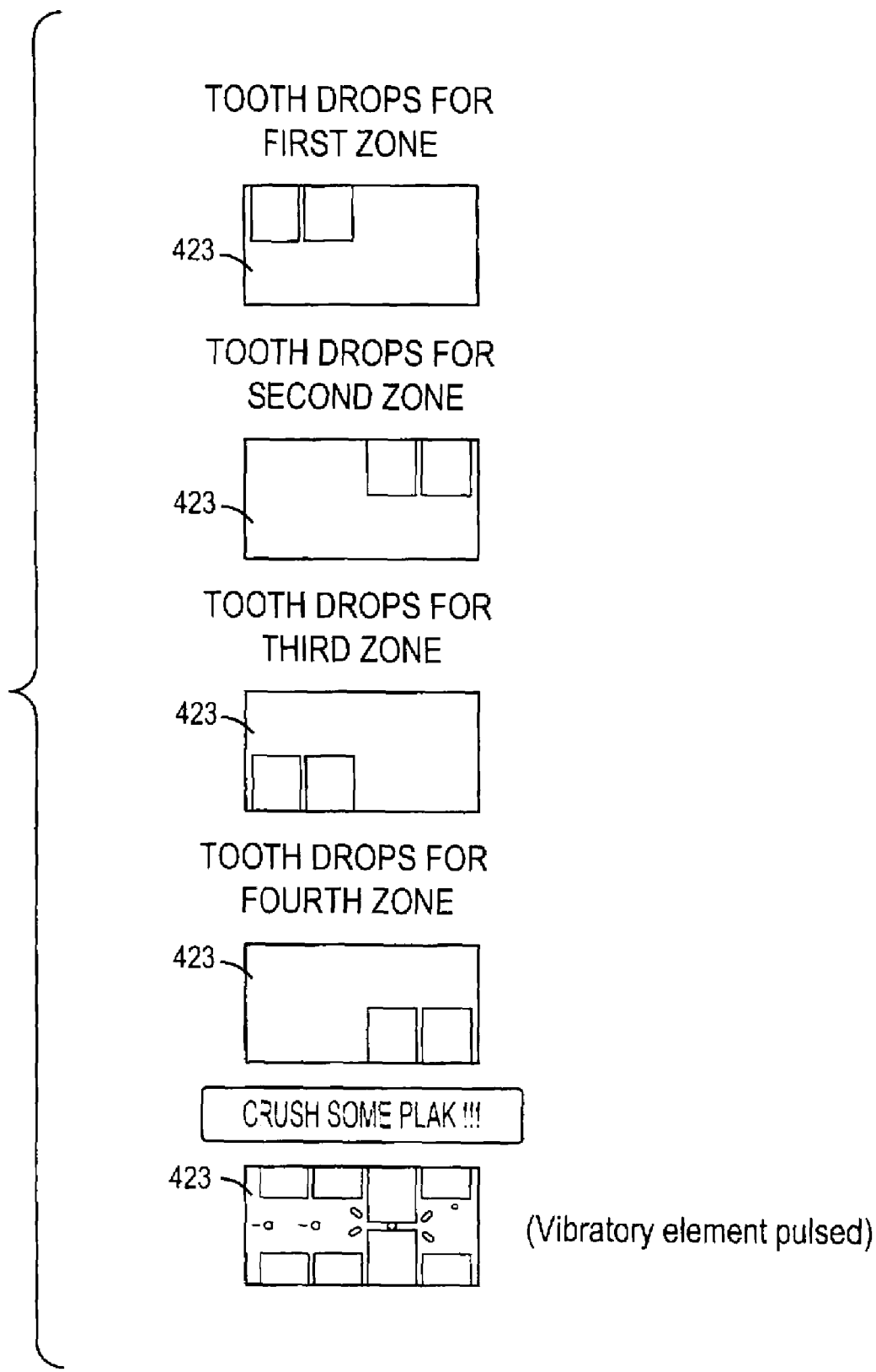
FIG. 5C is a schematic illustration of objects displayed during tooth brushing with the embodiment of FIGS. 5A and 5B.

FIGS. 5A-5C illustrate a toothbrush 401 according to yet another embodiment. Toothbrush 401 includes a display screen 423, game controllers 430A and 430B, a handle 410, a head 412 and cleaning elements 416 (e.g., bristles), as well an internal vibratory element (not visible in FIGS. 5A and 5B). In the embodiment of FIGS. 5A and 5B, brushing zones are indicated by graphical objects at different locations on a display screen 423. As shown in FIG. 5C, for example, during a first interval two rectangles can be displayed in the upper left corner of the display screen 423 to represent a first brushing zone, e.g., front teeth. Successive intervals are indicated by displaying similar rectangles in the upper right, lower left and lower right corners of the display screen 423. At the conclusion of brushing, the display screen 423 displays a game, which can include the same graphical objects used during the brushing intervals. For example, the user can select a set of upper and lower "teeth" using one controller 430A, and use another controller 430B to cause the selected "teeth" to converge in an attempt to trap an object (e.g., simulating plaque) therebetween. Upon successfully trapping the virtual plaque between the virtual teeth, the vibratory element is pulsed to provide haptic feedback. In this way, incorporating educational oral care concepts into virtual graphical entities that the player can control has the effect of making the game play more engaging and entertaining to promote good oral hygiene habits.

Figure 6A:
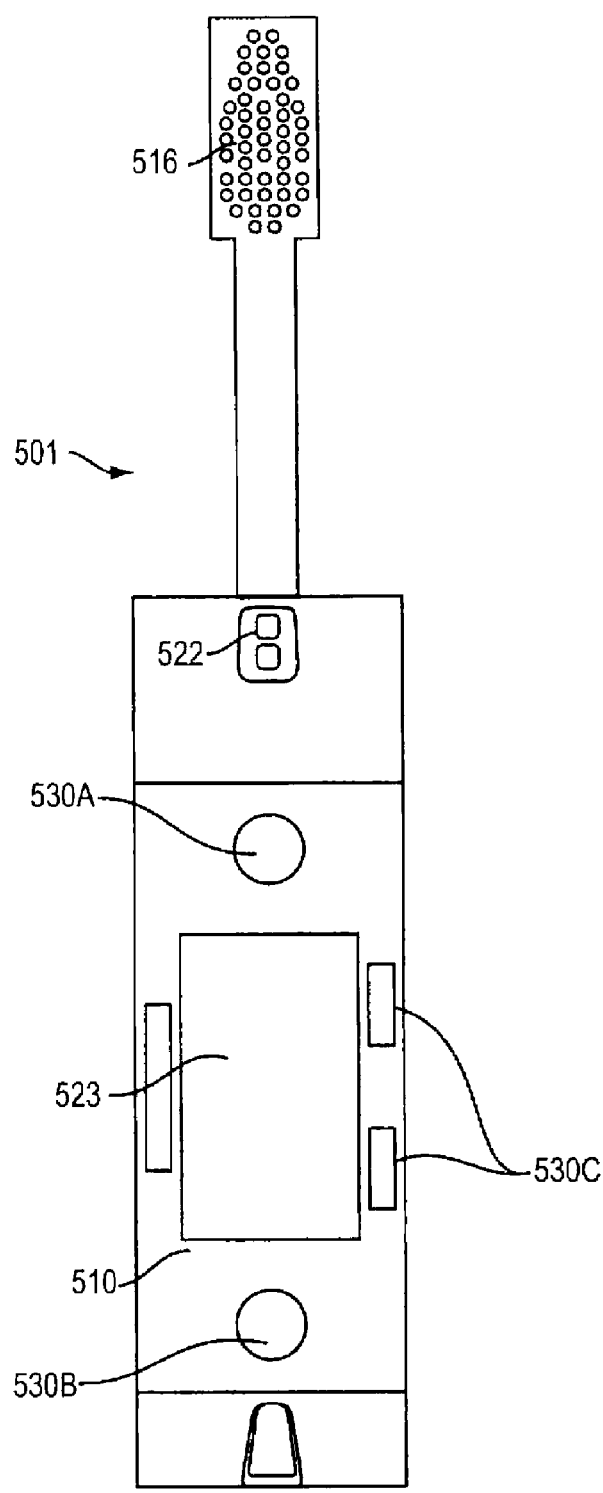
FIGS. 6A and 6B are front and side views, respectively, of a toothbrush according to another embodiment.
Figure 6B:
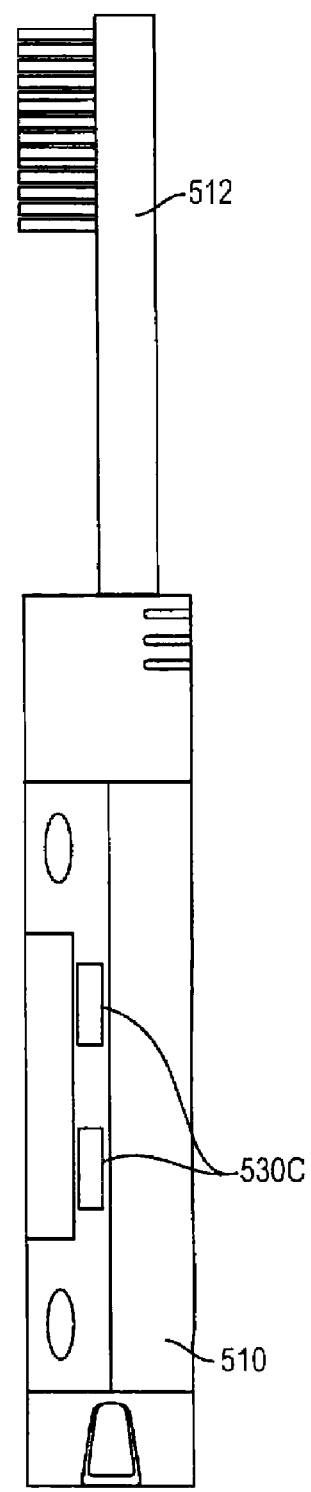
Figure 6C:
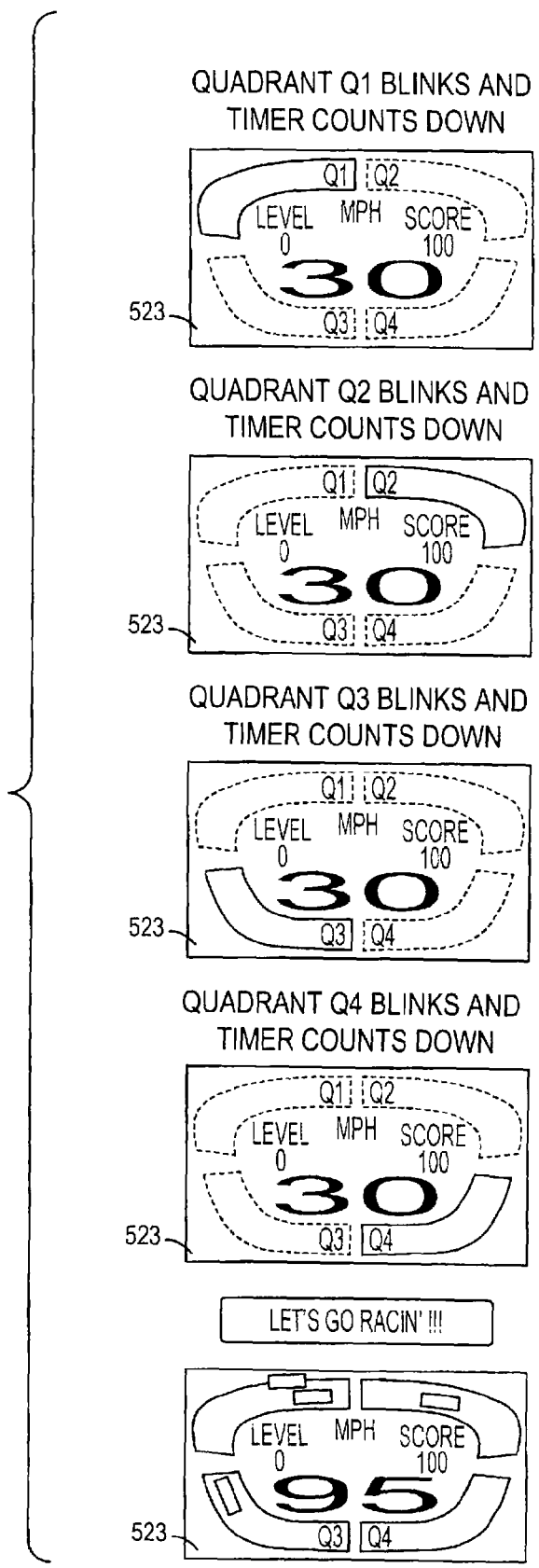
FIG. 6C is a schematic illustration of objects displayed during tooth brushing with the embodiment of FIGS. 6A and 6B.

In the embodiment of FIGS. 6A-6C, toothbrush 501 includes a display screen 523, game controllers 530A and 530B, a handle 510, a head 512 and cleaning elements 516 (e.g., bristles), as well an internal vibratory element (not visible in FIGS. 6A and 6B). Display screen 523 includes four quadrants around its periphery (see FIG. 6C) to indicate four brushing zones. The quadrant corresponding to the current interval of the brushing regimen is highlighted (shown as a sold line in FIG. 6C). The center portion of the display can be used to display the time (e.g., seconds) remaining in the brushing interval. At the conclusion of brushing, the display can be converted into a game, for example, in which the peripheral quadrants are together used as a racetrack around which cars race. The user can control the motion of the car using controls 530A and 530B. Additional game controls 530C optionally can be provided, or areas 530C optionally can be molded as non-functional decorative detail. As in other embodiments, the vibratory element may also be incorporated into the game. For example, game controls 530C could be used to increase or decrease the speed of the virtual race car. The vibratory element could then be operated at lower rates to correspond to slower racing speeds and at higher rates to correspond to higher racing speeds.

Figure 7A:
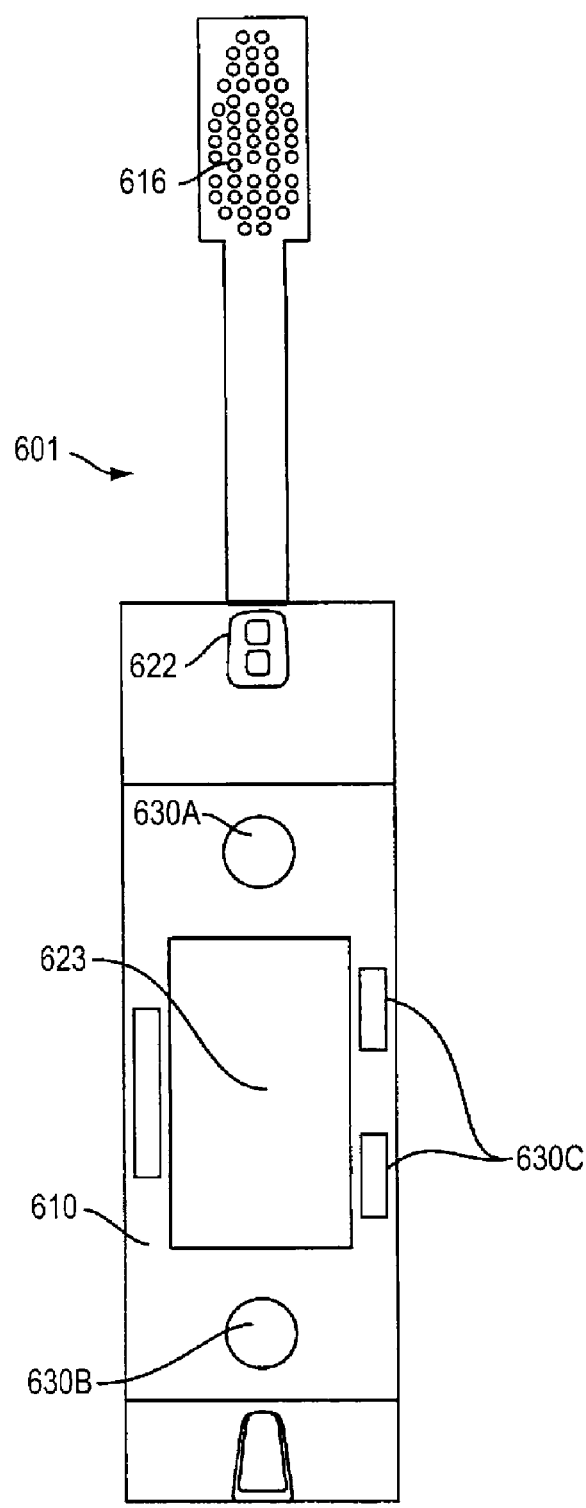
FIGS. 7A and 7B are front and side views, respectively, of a toothbrush according to another embodiment.
Figure 7B:
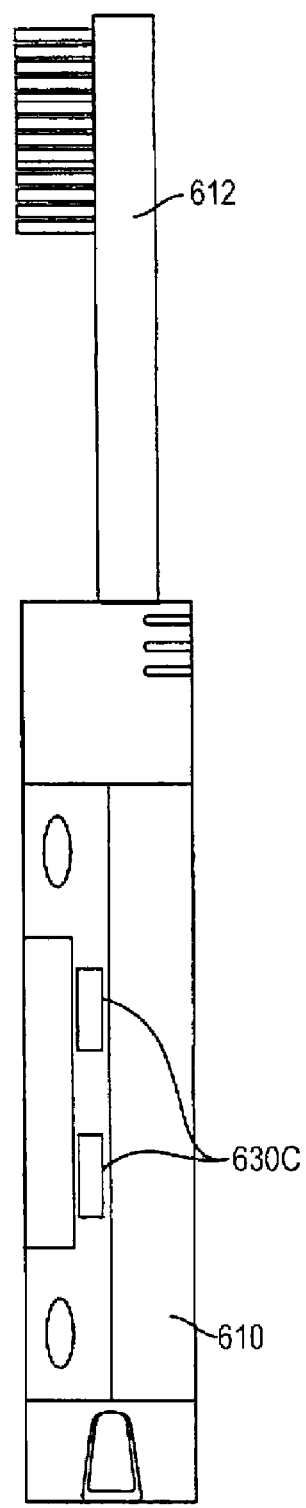
Figure 7C:
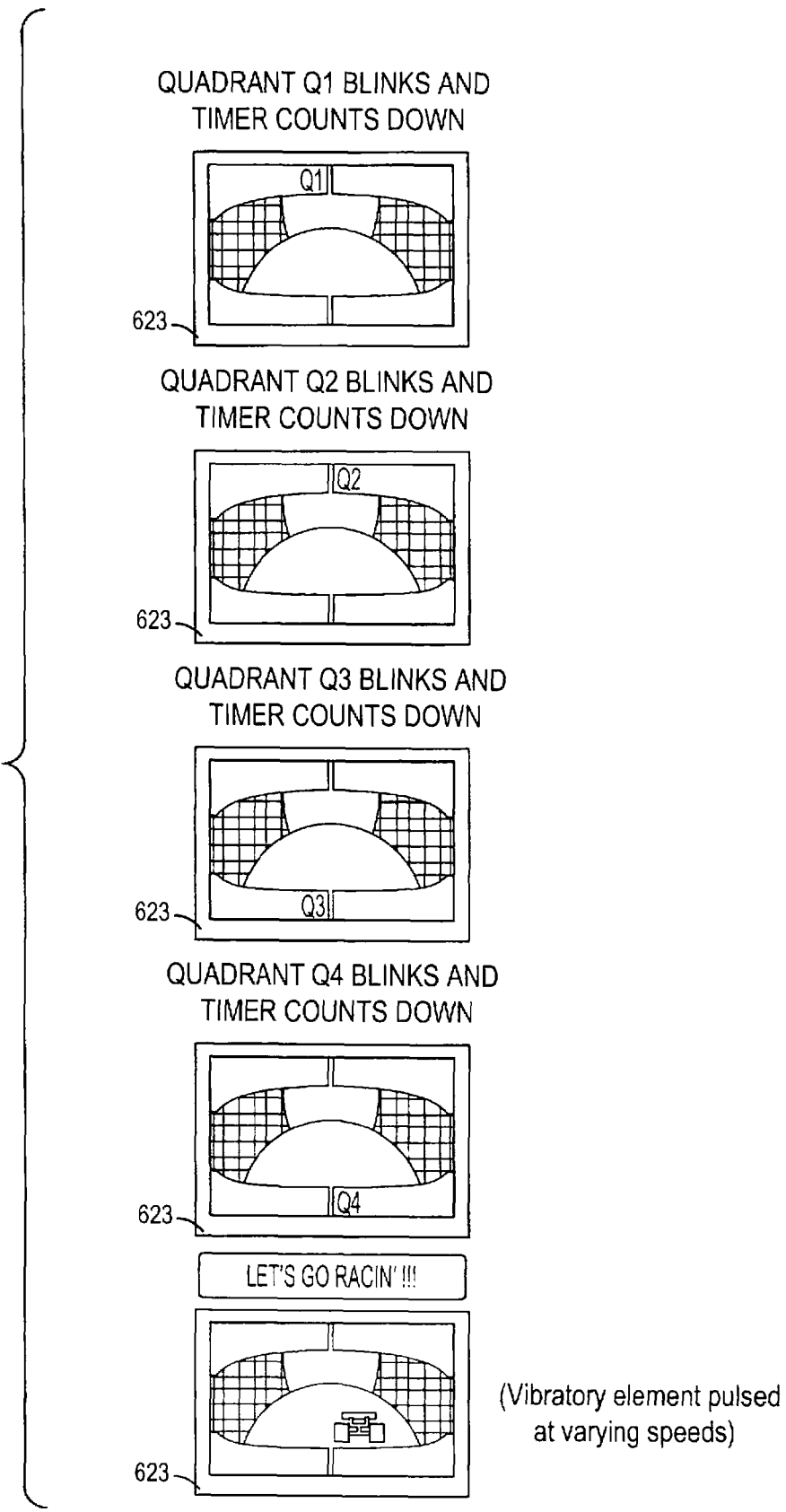
FIG. 7C is a schematic illustration of objects displayed during tooth brushing with the embodiment of FIGS. 7A and 7B.

FIGS. 7A-7C show a toothbrush 601 according to another embodiment. Toothbrush 601 includes a display screen 623, game controllers 630A-630C, a handle 610, a head 612 and cleaning elements 616 (e.g., bristles), as well an internal vibratory element (not visible in FIGS. 7A and 7B). Toothbrush 601 represents another embodiment of a toothbrush in which four peripheral quadrants on the display screen simulate groups of teeth, as shown in FIG. 7C. A semicircular shaped object between the quadrants represents a tongue. During brushing, the display screen 623 may display a timer indicating the time remaining in each brushing interval as well as an indicator in the quadrant to be brushed in the current interval. At the conclusion of brushing, the display screen 623 displays a race car, which the user controls via controllers 630A, 630B and optionally 630C. The game can utilize some or all of the same graphical objects displayed during brushing, and the vibratory element can be activated at varying rates to simulate the speed of a race car.

Figure 8A:
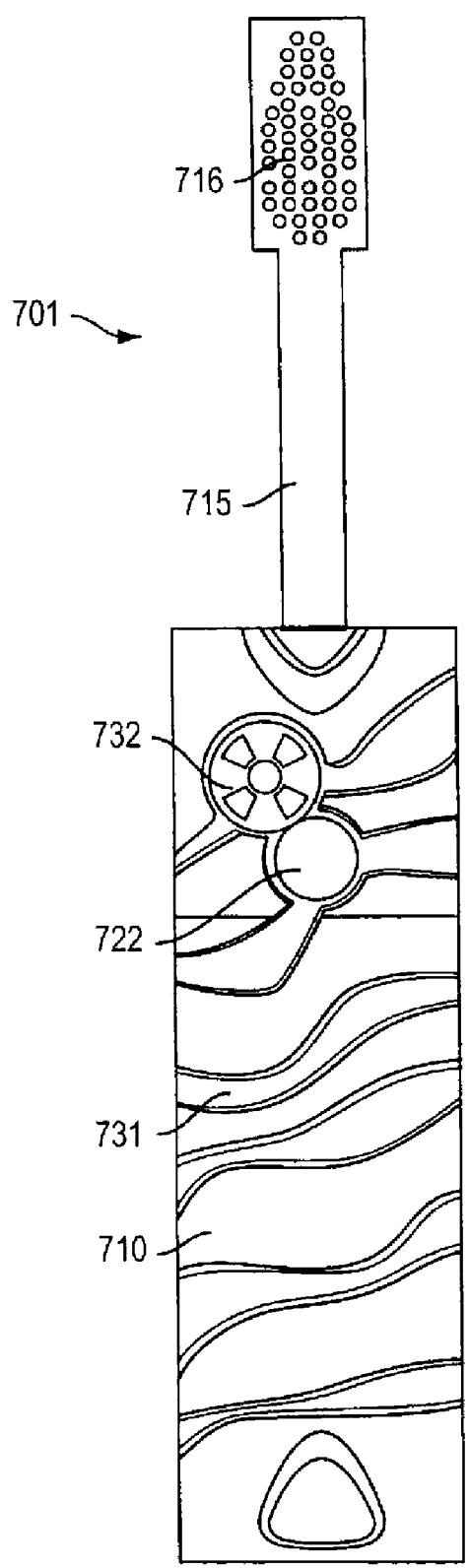
FIGS. 8A and 8B are front and side views, respectively, of a toothbrush according to another embodiment.
Figure 8B:
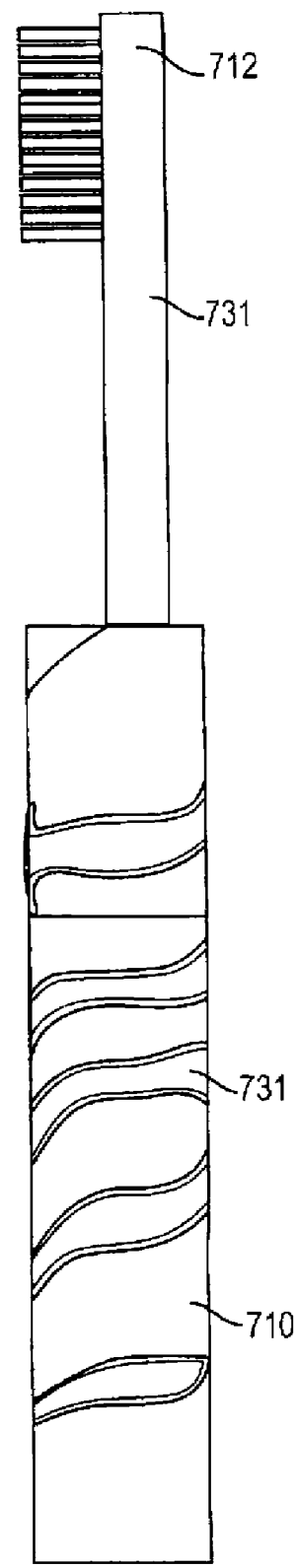

FIGS. 8A and 8B show a toothbrush 701 according to another embodiment. Toothbrush 701 includes a translucent neck portion 715, under which a plurality of differently colored light emitting diodes (LEDs) are located. Toothbrush 701 includes a handle 710, a head 712 and cleaning elements 716 (e.g., bristles), as well an internal vibratory element (not visible in FIGS. 8A and 8B). After the user presses button 722, the vibratory element is activated, and successive brushing zones are indicated by illuminating one of the LEDs in neck 715 (e.g., 30 seconds blue, 30 seconds red, 30 seconds green, then 30 seconds pink). At the conclusion of brushing, the LEDs can be illuminated in a random sequence, for example, to signal that brushing has been completed. Optionally, a speaker 732 may provide voice instructions during the respective intervals (e.g., "start brushing," "brush front teeth," "brush upper molars," etc.). At the conclusion of brushing, the speaker can play music or give a congratulatory message.

Figure 9A:
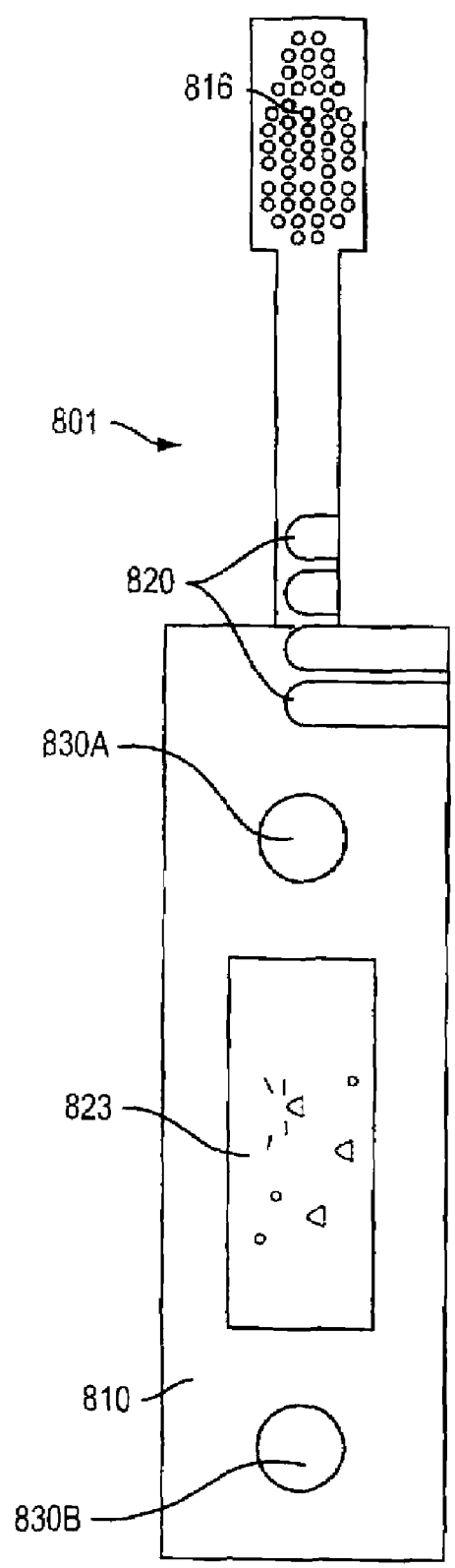
FIGS. 9A and 9B are front and side views, respectively, of a toothbrush according to another embodiment.
Figure 9B:
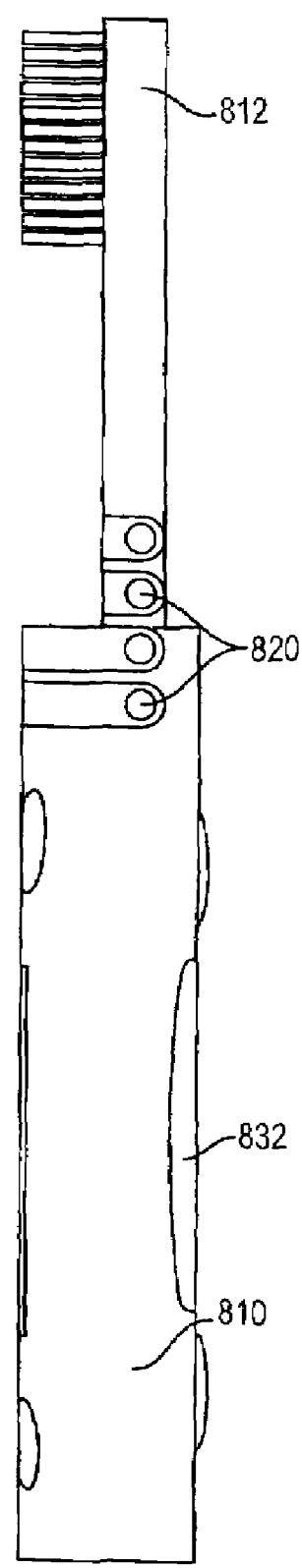

FIGS. 9A and 9B show a toothbrush 801 according to another embodiment. Toothbrush 801 includes a display screen 823, game controllers 830A and 830B, a handle 810, a head 812 and cleaning elements 816 (e.g., bristles), as well an internal vibratory element (not visible in FIGS. 9A and 9B). A plurality of indicator lights 820 are illuminated during respective intervals for sequential brushing zones. A display screen 823 can be used to display text for each of the brushing zones (e.g., "front teeth," "upper molars," etc.) during the respective interval. The indicator lights 820 can blink randomly at the conclusion of brushing to signal that brushing has been completed. Following brushing, the display screen 823 can be used to display a game that the user controls via controllers 830A and 830B.

Either of algorithms 84 (FIG. 2C) or 86 (FIG. 2D) can be adapted to toothbrushes 201, 301, 401, 501, 601 or 801. Either of algorithms 80 (FIG. 1C) or 82 (FIG. 1D) can be adapted to toothbrush 701. Such adaptations are within the routine ability of a person of having ordinary skill in the art (once such a person is provided with the information contained herein), and are therefore not discussed further.

Optionally, any of the toothbrushes described above may include a motion sensor. A logic circuit can be programmed to shut power off, pause a timer, or take other suitable action in the event the toothbrush is not oscillated in a brushing motion for more than a threshold period of time, e.g., 3-5 seconds. This can help prevent a child from merely watching the light displays or playing the games without actually brushing his or her teeth. In addition, a motion sensor can help preserve battery life by automatically shutting power off when the toothbrush is not in use.

Similarly, any of the above-described toothbrushes may have a speaker and a suitable audio driver. An audible signal can announce the brushing zone. This may be particularly desirable in embodiments where the visual display(s) are not as easily seen by the user while brushing. The audible signal can be a sound such as beep or chime, which may or may not be distinct for each brushing zone, or may be a voice that announces a brushing zone ("start brushing," "brush front teeth," "brush upper molars," "brush lower molars," "brush tongue," "done," etc.). Optionally, the toothbrush may have mute button to toggle sound on and off.

As described above, the games can utilize the graphic objects or images used during the brushing intervals, e.g., images or objects representing or depicting the mouth, teeth, gums, tongue, etc. Such games can encourage good oral hygiene, such as by having as an object of the game removal of plaque from teeth. In addition, having a mouth, teeth or the like as scenery or background in a game can help draw attention to the user's teeth and need for oral care.

A wide variety of games can be programmed. For example, an "electronic pet" such as a Tamagotchi pet or NeoPet can be programmed. Generally, such games require the user to "feed" the pet, which enables the pet to evolve into a wide range of characters, depending on how well the user cares for the pet. If the pet is not adequately "nourished," it may lose strength and its evolution into the characters can be inhibited.

Figure 10:
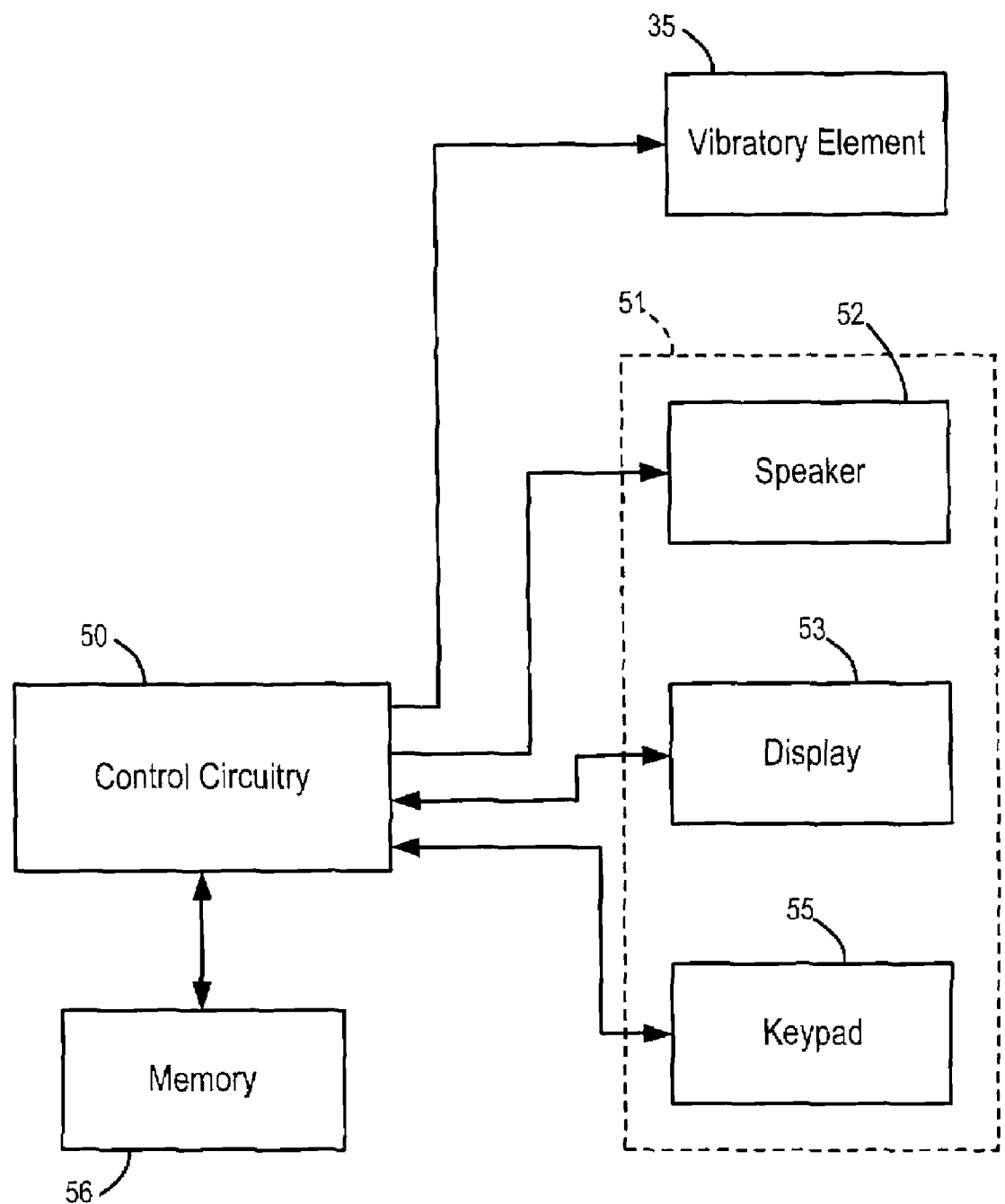
FIG. 10 is a schematic representation of internal components of toothbrushes according to at least some embodiments.

FIG. 10 is a block diagram of control circuitry, memory and other components that can be used to implement various aspects of the above-described embodiments. As shown in FIG. 10, a toothbrush may include electronic components and application programs including a user interface 51, control circuitry 50 and a memory 56. User interface 51 provides audio and/or visual signals to a user and enables a user to interact with the toothbrush electronic components. The user interface 51 is operatively connected to the control circuitry 50. The user interface 51 may optionally include a speaker 52, a display device 53 (e.g., one of the display devices 123, 323, 423, 523, 623 or 823 and/or lighted regions 20A-20E, 120A-120D, 220A-220D or 820 described above) and a keypad or button arrangement 55 (e.g., various ones of buttons 22, 122, 130A, 130B, 220A-220D, 222, 322, 330A, 330B, 422, 430A, 430B, 522, 530A, 530B, 530C, 622, 630A, 630B, 630C, 722, 822, 830A and 830B described above). The speaker 52 provides audible signals to user. The display device 53 provides visual signals to the user in the form of alphanumeric characters, colors or graphical symbols. The display device 53 may be a device used for computing devices, such as a liquid crystal display (LCD). The control circuitry 50, which may include a microprocessor (not shown) for use with digital data, is also operationally connected to vibratory element 35. Control circuitry 50 can thus turn vibratory element 35 on and off (and vary the speed of vibratory element 35 in some embodiments).

The control circuitry 50 is also operatively coupled to memory 56. Memory 56 stores data installed or programmed by the user, including instructions for implementing control of the toothbrush during a brushing regimen and instructions for one or more games. Memory 56 may be any programmable type in which nonvolatile storage can be electrically erased and reprogrammed. Possible alternatives include flash memory, flash ROM, RAM with battery backup. It should be understood that a game episode formatted for a toothbrush may be downloaded to memory 56 or a game episode may be preloaded in the memory.

In one arrangement, memory 56 may be insertable in the control circuitry 104 so that various game programs can be interchangeably played with the same toothbrush. This embodiment memory 106 comprises a memory module with a housing, such as Compact Flash, Secure Digital Media and the like. The handle 10 may have a slot for receiving and retaining an insertable memory module. In this way, a toothbrush provides an oral care platform for expansion of games and other programming related to or associated with oral care. Nevertheless, the games could have entertaining value other than oral care.

Figure 11A:
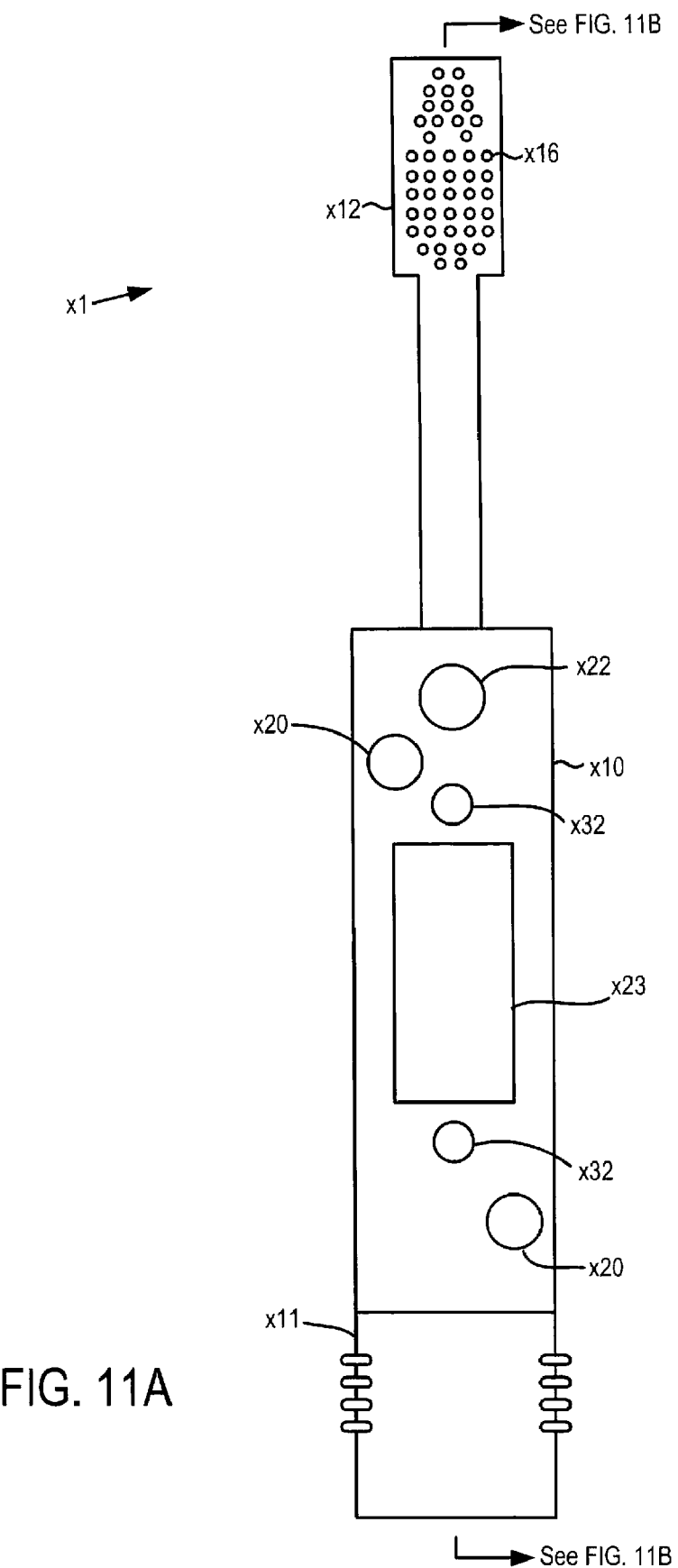

FIGS. 11A-11C illustrate various internal components of toothbrushes according to at least some embodiments. FIGS. 11A-11C will be used to describe arrangements of internal components that may apply to any of the embodiments described above. Accordingly, and to indicate the relationship of various components in FIGS. 11A-11C to similar components in the above-described embodiments, certain reference numbers in FIGS. 11A-11C are prefaced with a "x." Thus, for example, toothbrush x1 of FIGS. 11A-11C corresponds generally to toothbrushes 1, 101, 201, 301, 401, 501, 601, 701 and 801 described above.

As seen in FIG. 11A, toothbrush x1 includes a handle x10, head x12 and bristles x16. Toothbrush x1 further includes at least one activating button x22, and may include a display screen x23, one or more lights x20, and/or one or more game controls x32. No attempt is made to show all of the possible display devices and other user interfaces from the previously-described embodiments in toothbrush x1. However, persons of ordinary skill in the art can readily understand (when provided with the information contained herein) how a toothbrush having one of the internal component arrangements shown in FIGS. 11A-11C can be adapted to include any of the features described in connection with previous embodiments.

FIG. 11B is a cross-sectional view of toothbrush x1 from the location shown in FIG. 11A. Handle x10 includes an end cap x11 which is removable from handle x10 to expose an internal cavity x13. Cavity x13 holds a battery x19 between two spring contacts. Battery x19 may include one or more standard "AA" size 1.5 volt batteries, although other types of batteries can also be used. Handle x10 further contains a circuit board x17. Circuit board x17 includes the control circuitry 50 and memory 56 described in connection with FIG. 10. Circuit board is electrically connected to battery x19, display x23, buttons x22 and x32, lights x20, and vibratory element x35. So as to avoid obscuring the drawing with unnecessary details, these electrical connections are omitted from FIG. 11B. However, persons of ordinary skill in the art will readily appreciate that such connections can be formed using wires, conductive traces and/or other known means.

As is also shown in FIG. 11B, vibratory element x35 is located in head x12. When activated, vibratory element x35 is powered by battery x19 (and controlled by electronics on circuit board x17) so as to induce vibrations in head x12 and thereby enhances teeth-cleaning action imparted by bristles x16. As described above, vibratory element x35 can also be used to enhance game playing experience and/or to signal different intervals of a brushing regimen.

Vibratory element x35 is a vibratory armature. In alternate embodiments, vibratory element x35 includes a micro motor attached to a shaft, with the shaft coupled to an eccentric rotating about an axis parallel to the longitudinal axis of the toothbrush. In still other embodiments, vibratory element x35 includes an eccentric that is driven by a micro motor in a translatory manner.

FIG. 11C is a cross-sectional view of a toothbrush x1'. Toothbrush x1' is similar to toothbrush x1, except that vibratory element x35' is located in a portion of the neck that precedes head x12'. Components x11', x12', x13', x16', x17', x19', x22', x23' and x32' in FIG. 11C are similar to components x11, x12, x13, x16, x17, x19, x22, x23 and x32, respectively, in FIG. 11B.

Figure 12:
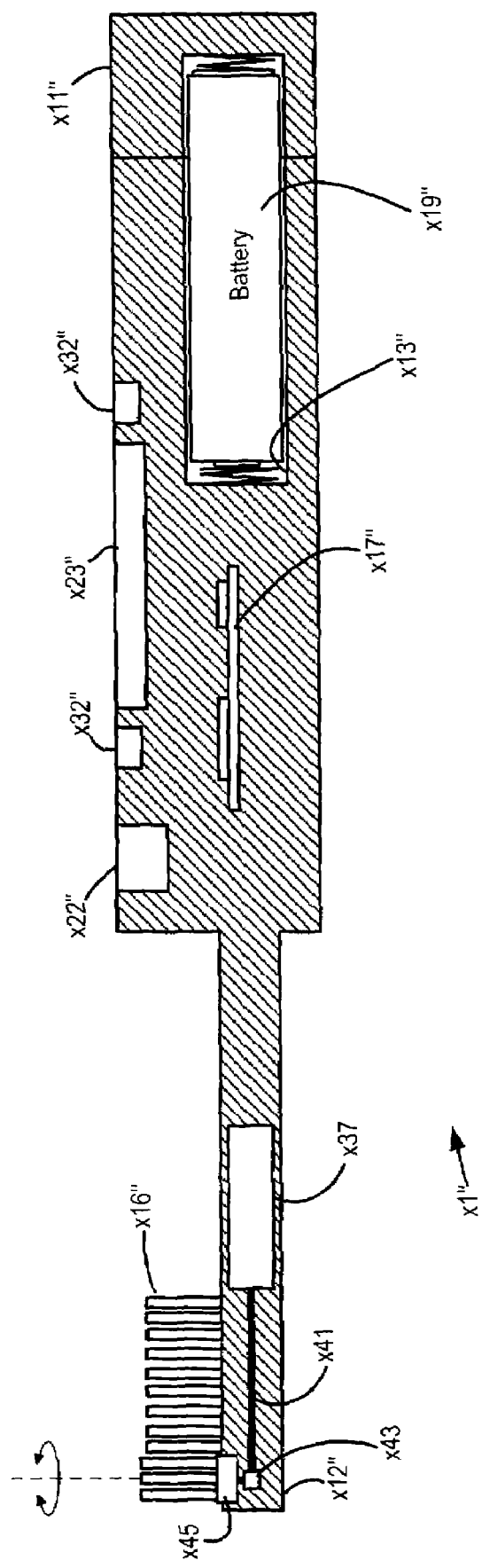
FIG. 12 is a cross-sectional view of a toothbrush, according to at least some alternate embodiments, having an oscillatory motion-inducing element.

FIG. 12 is a cross-sectional view of a toothbrush x1" according to at least some additional embodiments. Instead of a vibratory element, toothbrush x1" includes a different type of motion-inducing element. In particular, a motor x37 causes a spindle x45 rotate in an oscillatory manor about the axis shown as a broken line. A subset of tooth cleaning elements x16" is located on spindle x45. A drive shaft x41 and a suitable connecting linkage x43 couple motor x37 to spindle x45. Linkages suitable for coupling a unidirectional rotary shaft output from a motor (such as motor x37) so as to provide oscillatory motion are known in the art and thus not further described herein. Toothbrush x1" can be configured to operate in a manner similar to any of the previously-described embodiments, except that oscillatory motion is implemented instead of vibratory motion. For example, motor x37 can be pulsed (or otherwise selectively activated) to indicate separate intervals of a brushing regimen and/or for incorporation into game play.

Additional embodiments of the invention include configurations of vibratory element(s), bristles (or other tooth cleaning elements) and other components as described in U.S. patent application Ser. No. 10/768,363 (filed Jan. 30, 2004 and titled "Toothbrush with Enhanced Cleaning Effects"), published as U.S. Pat. Pub. No. 20050091769A1, now U.S. Pat. No. 7,703,163, incorporated by reference herein. For example, the neck portion of the toothbrush can be provided with neck-part zones made of an elastically relatively compliant material so as to increase the elasticity of the neck part. This would permit the head, during use of the toothbrush, to be forced back resiliently in the case of forces acting in the direction of the brushing surface. Optionally, the neck-part zones could be designed as notches which extend over part of the neck circumference and are filled with elastically compliant material (e.g. with thermoplastic elastomer).

The handle of a toothbrush according to various embodiments (including the embodiments described above) may be designed to enable the user to easily grip and manipulate the toothbrush. More particularly, the handle may be shaped and/or include ergonomic features to provide a higher degree of control for the user while maintaining comfort. Examples of ergonomic features include an overmolded grip portion that can be segmented and ergonomically sized for users. The handle may include sections that are angled relative to each other and/or which are wider or narrower than other portions of the handle to provide increased control and comfort during use. In the embodiment shown in FIGS. 8A and 8B, for example, a textured grip portion 731 can be provided to provide a non-slip surface for the user to grip the toothbrush. The grip portion 731 can be provided on the same side of the handle as the bristles, on the opposite side of the handle as the bristles, or around the circumference of the handle as shown in FIGS. 8A and 8B. As shown in FIG. 8B, the elastomeric portion 731 also may be included on the side of head 712 opposite bristles 716, e.g., for aesthetic purposes or the like.

The head, bristles and any other tooth cleaning components of toothbrushes according to various embodiments can be ergonomically sized and shaped to facilitate tooth cleaning, including interproximal tooth cleaning. The head can be generally elliptical or rectangular in shape, for example, although other configurations are contemplated. The bristles generally extend from the surface of head and can be of conventional size and spacing for effective tooth cleaning. A pick (not shown) optionally can be included and may have a size and conical shape adapted to promote interproximal cleaning effectiveness.

The head may integral with or permanently attached to the handle, or may be replaceable. One or more other oral surface engaging elements, such as a flossing element, plaque scrapper, elastomeric massaging elements, and the like, may also be present on the toothbrush. In practice, the toothbrush can have these any of these features alone or in any combination with other features not illustrated herein. It will also be appreciated that while the cleaning elements are illustrated herein as tufts of bristles, other cleaning elements of varying size, shape, cross-section and material may be used.

The toothbrush may have concave molded portions for holding and dispensing fragrance, flavorants, actives or other materials. For example, a plurality of sockets (not illustrated) may be located at one or both ends of the handle. The sockets can be sized and shaped to releasably hold fragrance, flavor-yielding capsules or other materials to be dispersed. For example, sockets can be molded from elastomeric material as concave hemispheres of suitable dimensions to enable flavor-yielding capsules to be easily dispensed and replaced. Alternatively, the sockets can be configured to hold commercially available fragrance or flavor yielding gel capsules.

The head may be rigid or flexible. An example of a toothbrush having a flexible head is found in U.S. Pat. No. 6,442,787, which is incorporated by reference. The toothbrush has first and second sections with an elastomer section (or joint) located therebetween. Other details of flexible toothbrush heads, as well as examples of other flexible head configurations which can be used, are described in US 2006/0117508 A1, which is hereby incorporated by reference.

The handle and head sections can be molded from a plastic or resin such as polypropylene. Grip portions 731 (FIGS. 8A and 8B), buttons, and various other components of the toothbrush can be formed from elastomer materials known to persons skilled in the art, such as propylene-ethylene copolymer elastomers. Elastomers can be used to form, for example, a handle or a portion thereof, a flexible joint in the head, a flexible pick, elastomeric cleaning elements, bristles, a tongue scraping element, other components of an oral care implement, or any combination thereof. The elastomers can be incorporated using conventional molding techniques well known to those of ordinary skill, such as overmolding or co-injection molding techniques.

In one embodiment, referring to FIGS. 1A-1B, a ratio of the length of the light areas 24 of neck and head 12 to the height of the toothbrush (measured from the distal bottom end of base to the distal top of head 12) ranges from 1:10 to 2:5. In another example, the noted neck/head length to the toothbrush height ratio ranges from 1:20 to 1:30. Nevertheless, other values of the noted ratios are possible. In one embodiment, the external height of the toothbrush ergonomically sized for a child ranges from about 160 mm to 200 mm. In other embodiments, the height of the toothbrush 1 ranges from about 160 mm to 194 mm; to less than 194 mm or 190 mm. Nevertheless, other heights of the toothbrush 1 are possible. In one embodiment, the width of the handle 10 can range between 19 mm to 28 mm. In another embodiment, the depth of the handle 10 ranges between 19 mm to 27 mm. In other embodiments, the depth ranges between 19 mm to 21 mm. In a cylindrical configuration, the handle 10 may have a diameter ranging from 19 mm to 28 mm. Nevertheless, other values are possible. These ergonomic configurations provides for a toothbrush 1 to have a neck/head length to reach within the depth of the oral cavity, while balancing the need for musculoskeletal strength of a child to manipulate the toothbrush. Accordingly, these configurations or combination thereof enable an easily maneuverable powered toothbrush for children.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention. While specific toothbrush configurations have been illustrated, the present invention is not limited to any of the aesthetic aspects shown and, in practice, may differ significantly from the illustrated configurations.

The invention claimed is:

1. An oral care implement, comprising:
   a handle;
   a head coupled to the handle and having tooth cleaning elements coupled thereto;
   a plurality of illuminating regions;
   an electrically powered motion-inducing element configured to generate motion in at least a portion of the tooth cleaning elements; and
   a processor electrically coupled to the illuminating regions and the motion-inducing element, wherein the processor is configured to:
   successively activate each of the illuminating regions for a prescribed time period corresponding to a predetermined brushing interval; and
   pulse the motion-inducing element between each of the prescribed time periods.

2. The oral care implement of claim 1, wherein each of the illuminating regions is activated during at least one of the prescribed time periods.

3. The oral care implement of claim 1, wherein the motion-inducing element is a vibratory element or an oscillatory element.

4. The oral care implement of claim 1, wherein the processor is configured to provide user entertainment upon successful completion of the prescribed time periods, said user entertainment incorporating selective activation of the motion-inducing element.

5. The oral care implement of claim 4, wherein the user entertainment is a game requiring user input.

6. The oral care implement of claim 4, wherein the user entertainment is an automated display of the illuminating regions.

7. The oral care implement of claim 1, further comprising a display showing a graphical representation of teeth and a tongue and having a first portion of the teeth or tongue shaded during a first one of the prescribed time periods.

8. The oral care implement of claim 7, wherein the graphical representation has a second portion of the teeth or tongue shaded during a second one of the prescribed time periods.

9. The oral care implement of claim 1, wherein the plurality of illuminating regions are activated in a blinking fashion at a conclusion of the prescribed time periods.

10. An oral care implement, comprising:
a handle;
a head coupled to the handle and having tooth cleaning elements coupled thereto;
a display;
an electrically powered motion-inducing element configured to generate motion in at least a portion of the tooth cleaning elements; and
a processor electrically coupled to the display and the motion-inducing element, wherein the processor is configured to:
cause at least one of text and graphics to be shown on the display during a brushing session;
provide user instructions regarding time periods for predetermined brushing intervals using at least one of the motion-inducing element and the display, the time periods combining to form the brushing session; and
display a game on the display with which a user interacts via controls, the game being distinct from the user instructions and initiating automatically upon successful completion of the brushing session, said game incorporating selective activation of the motion-inducing element by pulsing the motion-inducing element upon successful completion of a game task.

11. The oral care implement of claim 10, wherein the motion-inducing element is a vibratory element.

12. The oral care implement of claim 10, wherein the motion-inducing element is an oscillatory element.

13. The oral care implement of claim 10, wherein the processor is configured to signal the user regarding the brushing intervals by showing material on the display comprising at least one of text and graphics on the display, the shown material providing indicia of segments of teeth and a tongue.

14. The oral care implement of claim 10, wherein the processor is configured to signal a user regarding completion of the brushing intervals by altering operation of the motion-inducing element.

15. The oral care implement of claim 14, wherein altering operation of the motion-inducing element comprises pulsing the motion-inducing element.

16. The oral care implement of claim 14, wherein altering operation of the motion-inducing element comprises varying a speed at which the motion inducing element is operated.

17. The oral care implement of claim 10, wherein the game comprises simulating use of a weapon and successful completion of the game task comprises destroying a simulated target with the simulated weapon.

18. The oral care implement of claim 17, wherein the user uses the controls to control movement and operation of the weapon.

19. The oral care implement of claim 18, wherein the game comprises simulating operation of a vehicle and in which the speed of operation of the motion-inducing element is varied in relation to a simulated speed of the simulated vehicle.

20. The oral care implement of claim 10, further comprising a plurality of illuminable segments in addition to the display, and wherein the implement is further configured to provide user instructions regarding the brushing intervals using the illuminable segments.

21. The oral care implement of claim 10, further including a neck disposed between to the handle and head, where a ratio defined by a length of the neck to a distal top of the head, to a length of a distal top to a distal bottom of the handle, ranges between 15% to 25%.

* * * * *